United States Patent [19]

Natarajan et al.

[11] Patent Number: 4,757,050
[45] Date of Patent: Jul. 12, 1988

[54] UREIDO RENIN INHIBITORS

[75] Inventors: Sesha I. Natarajan, Neshanic Station; Denis E. Ryono, Princeton; Edward W. Petrillo, Jr., Pennington, all of N.J.

[73] Assignee: E. R. Squibb Sons, Inc., Princeton, N.J.

[21] Appl. No.: 93,080

[22] Filed: Aug. 28, 1987

Related U.S. Application Data

[63] Continuation of Ser. No. 923,780, Oct. 27, 1986, abandoned, which is a continuation-in-part of Ser. No. 812,561, Dec. 23, 1985, abandoned.

[51] Int. Cl.$^4$ .............. A61K 37/02; C07K 7/02; C07K 5/08; C07K 5/10; C07K 7/06
[52] U.S. Cl. .............................. 514/18; 514/16; 514/17; 530/328; 530/329; 530/330; 530/331
[58] Field of Search ............... 530/328, 329, 330, 331; 514/16, 17, 18

[56] References Cited

U.S. PATENT DOCUMENTS

| | | | |
|---|---|---|---|
| 4,477,441 | 10/1984 | Boger et al. | 514/11 |
| 4,514,391 | 4/1985 | Gordon et al. | 524/2 |
| 4,548,926 | 10/1985 | Matsueda et al. | 514/19 |
| 4,599,198 | 7/1986 | Hoover | 530/333 |
| 4,616,088 | 10/1986 | Ryono et al. | 546/336 |
| 4,668,769 | 5/1987 | Hoover | 530/331 |
| 4,668,770 | 5/1987 | Boger et al. | 530/331 |

FOREIGN PATENT DOCUMENTS

| | | |
|---|---|---|
| 104041 | 3/1984 | European Pat. Off. |
| 8403044 | 8/1984 | PCT Int'l Appl. |
| 114993 | 8/1984 | European Pat. Off. |

*Primary Examiner*—Delbert R. Phillips
*Assistant Examiner*—Nathan M. Nutter
*Attorney, Agent, or Firm*—Lawrence S. Levinson; Stephen B. Davis

[57] ABSTRACT

Compounds of the formula

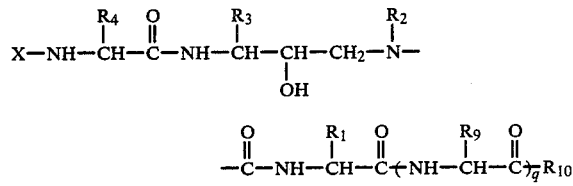

are disclosed. These compounds intervene in the conversion of angiotensinogen to angiotensin II by inhibiting renin and thus are useful as antihypertensive agents.

20 Claims, No Drawings

UREIDO RENIN INHIBITORS

RELATED APPLICATION

This application is a continuation of Ser. No. 923,780 filed on Oct. 27, 1986, now abandoned, which is a continuation-in-part of Ser. No. 812,561 filed on Dec. 23, 1985, now abandoned.

BACKGROUND OF THE INVENTION

Jones et al. in No. WO 84/03044 disclose renin inhibiting tetra-, penta-, or hexapeptide analogues of the formula $$X-D-E-A-B-Z-W$$

where X and W are terminal groups; D, E, B and Z, of which any one or, except with reduced analogues, two may be absent, are aromatic, lipophilic or (in the case of E) aromatic, lipophilic, or basic amino acid or amino acid analogue residues, and A is an analogue of a lipophilic or aromatic dipeptide residue wherein the peptide link is replaced by one to four-atom carbon or carbon-nitrogen link which is such or in hydrated form is an unhydrolyzable tetrahedral analogue of the transition state of the peptide bond as given above. In particular, A is defined as

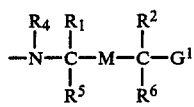

wherein M can be —CH—OH.

Szelke et al. in Eurpean Patent Application No. 104,041 disclose renin inhibitory polypeptides including the partial sequence $$X-A-B-Z-W$$

and $$X-Phe-His-A-B-Z-W$$

wherein A is

and G is

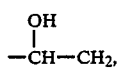

X is hydrogen, protecting group, or an amino acyl residue, B is a lipophilic amino acyl residue, and Z plus W are an amino alcohol residue or Z is aminoacyl and W is hydroxy, ester, amide, etc.

Matsueda et al. in U.S. Pat. No. 4,548,926 disclose renin inhibiting peptides of the formula

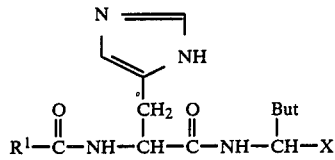

wherein But represents an isobutyl or sec-butyl group and X includes a group of the formula —CH($R^2$)—Y.

Gordon et al. in U.S. Pat. No. 4,514,391 discloses hydroxy substituted peptide compounds of the formula

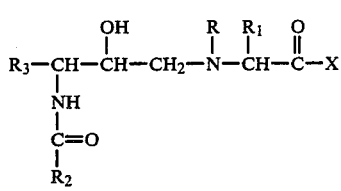

which possess angiotensin converting enzyme or enkephalinase inhibition activity.

SUMMARY OF THE INVENTION

This invention is directed to new hydroxy containing ureido renin inhibitos of formula I including pharmaceutically acceptable salts thereof

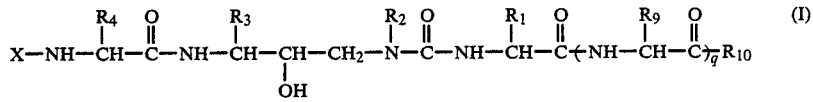

X is

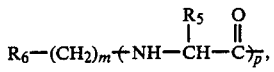

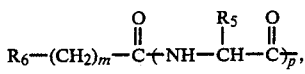

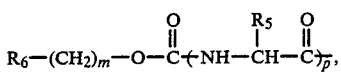

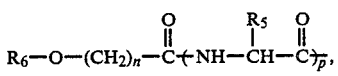

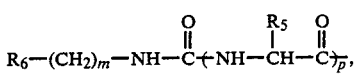

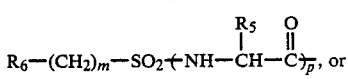, or

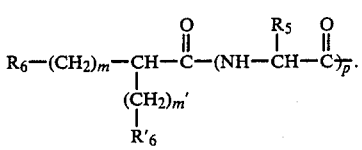

$R_1$, $R_3$, $R_4$, $R_5$, and $R_9$ are independently selected from hydrogen, lower alkyl, halo substituted lower alkyl, —(CH$_2$)$_n$-aryl, —(CH$_2$)$_n$-heterocyclo, —(CH$_2$)$_n$—OH, —(CH$_2$)$_n$—NH$_2$, —(CH$_2$)$_n$—SH, —(CH$_2$)$_n$—S-lower alkyl, —(CH$_2$)$_n$—O-lower alkyl, —(CH$_2$-

$)_n$—O—$(CH_2)_g$—OH,    —$(CH_2)_n$—O—$(CH_2)_g$—$NH_2$,
—$(CH_2)_n$—S—$(CH_2)_g$—OH,

—$(CH_2)_n$—S—$(CH_2)_g$—$NH_2$,

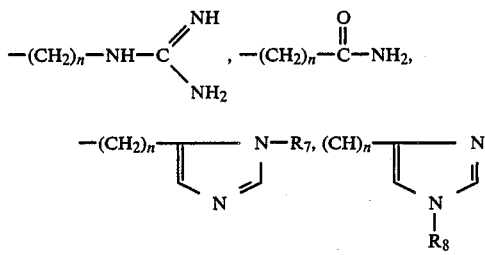

and —$(CH_2)_n$-cycloalkyl $R_2$ is hydrogen, lower alkyl, —$(CH_2)_m$-aryl, —$(CH_2)_m$-cycloalkyl, or —$(CH_2)_n$-heterocyclo.

$R_6$ and $R'_6$ are independently selected from lower alkyl, cycloalkyl, aryl and heterocyclo.

p is zero or one.

m and m' are independently selected from zero and an integer from 1 to 5.

n is an integer from 1 to 5.

g is an integer from 2 to 5.

$R_7$ is

$R_8$ is 2,4-dinitrophenyl,

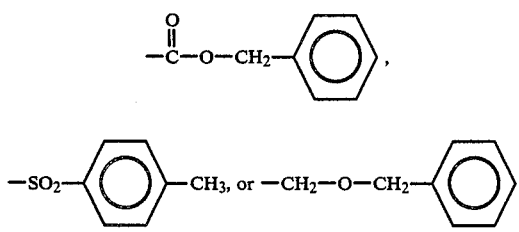

q is zero or one.

$R_{10}$ is hydroxy, —O—lower alkyl, —O—$(CH_2)_m$-cycloalkyl, —O—$(CH_2)_m$-aryl, —O—$(CH_2)_n$-heterocyclo, —$NH_2$, or —O—salt forming ion.

DETAILED DESCRIPTION OF THE INVENTION

This invention in its broadest aspects relates to the compounds of formula I above, to compositions and the method of using such compounds as antihypertensive agents.

The term lower alkyl used in defining various symbols refers to straight or branched chain radicals having up to seven carbons.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are selected from methyl, methoxy, methylthio, halogen, and hydroxy.

The term heterocyclo refers to fully saturated or unsaturated rings of 5 or 6 atoms containing one or two O and S atoms and/or one to four N atoms provided that the total number of hetero atoms in the ring is 4 or less. The heterocyclo ring is attached by way of an available carbon atom. Preferred heterocyclo groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms as defined above is fused to a benzene ring. The preferred bicyclic ring is indolyl.

The compounds of formula I wherein X is

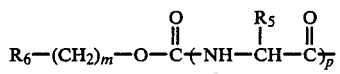

can be prepared by coupling an alcohol of the formula

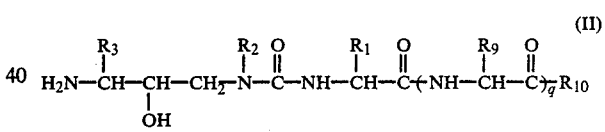

with a peptide of the formula

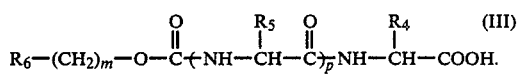

This reaction is preferably performed in a solvent such as dimethylformamide and in the presence of hydroxybenzotriazole, diisopropylethylamine, and a coupling agent such as dicyclohexylcarbodiimide.

The corresponding compounds of formula I wherein p is zero can be prepared by coupling the alcohol of formula II with the amino acid of the formula

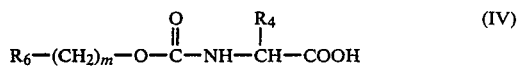

to yield the products of the formula

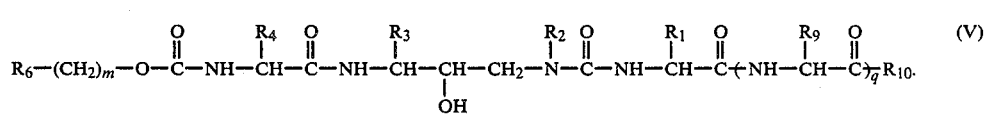

When $R_6-(CH_2)_m-$ is t-butyl or benzyl, then the product of formula V can be treated so as to remove the t-butoxycarbonyl or benzyloxycarbonyl group such as by the use of hydrochloric acid when $R_6$ is t-butyl to yield the amine of the formula

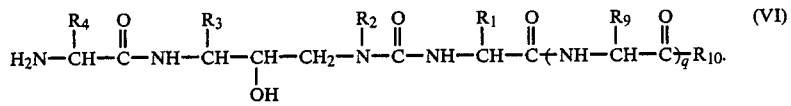

Coupling with the amino acid of the formula

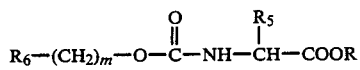 (VII)

yields the products of formula I wherein p is one.

The compounds of formula I wherein X is other than

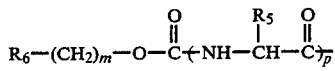

can be prepared by treating the product of formula I wherein $R_6$ is

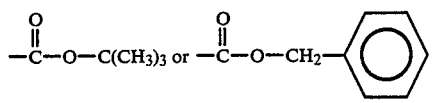

and m is zero to remove the t-butoxycarbonyl or benzyloxycarbonyl group and yield the intermediate of the formula

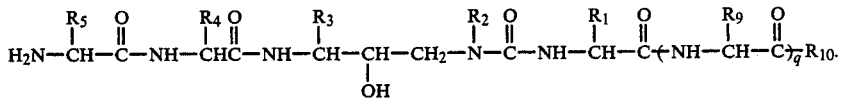 (VIII)

The amine of formula VIII or formula VI is treated with the halide of the formula $R_6-(CH_2)_m$-halo (IX)

particularly where halo is Br to give the products of formula I wherein X is

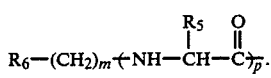

The amine of formula VIII or VI is treated with the acid chloride of the formula $$R_6-(CH_2)_m-\overset{O}{\underset{\|}{C}}-Cl \text{ or}$$ (X)

$$R_6-O-(CH_2)_n-\overset{O}{\underset{\|}{C}}-Cl$$ (XI)

in the presence of triethylamine to yield the products of formula I wherein

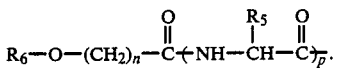

The amine of formula VIII or VI is treated with the substituted sulfonyl chloride of the formula $R_6-(CH_2)_m-SO_2-Cl$ (XII)

to yield the products of formula I wherein X is

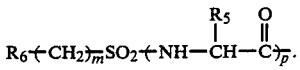

The amine of formula VIII or VI is treated with phosgene and the resulting acid chloride is treated with the substituted amine of the formula $R_6-(CH_2)_m-NH_2$ (XIII)

to yield the products of formula I wherein X is

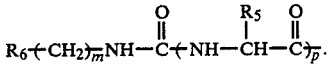

The products of formula I wherein X is

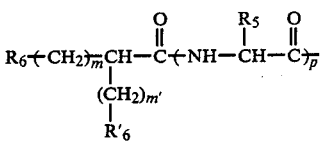

can be prepared by coupling the carboxylic acid of the formula

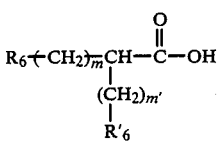 (XIV)

to the amine of formula VI or VIII in the presence of dicyclohexylcarbodiimide and 1-hydroxybenzotriazole hydrate. Alternatively, the acid of formula XIV can be converted to the acid chloride and this acid chloride can then be coupled to the amine of formula VI or VIII in the presence of triethylamine and tetrahydrofuran or water and sodium bicarbonate.

The alcohol of formula II can be prepared by reacting an alcohol of the formula (XV)

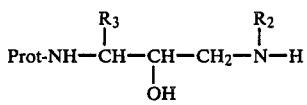   (XV)

preferably the hydrochloride salt thereof, with the carbamoyl chloride of the formula

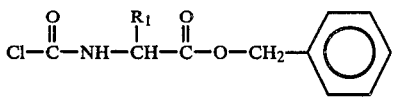   (XVI)

to give

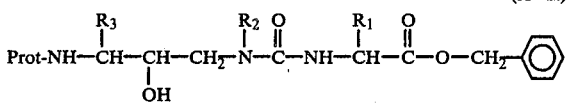   (XVII)

wherein Prot is an amino protecting group such as t-butoxycarbonyl. Removal of the benzyl group from the intermediae of formula XVII such as by hydrogenation yields the acid of the formula

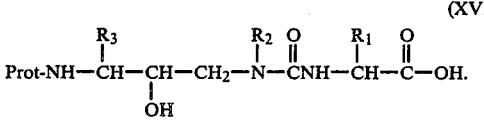   (XVIII)

Removal of the t-butoxycarbonyl amino protecting group such as by treatment with hydrochloric acid gives the alcohol of formula II wherein q is zero and $R_{10}$ is hydroxy. When q is zero and $R_{10}$ is other than hydroxy, the acid of formula XVIII is treated to introduce the $R_{10}$ group, for example, treatment with diazomethane where $R_{10}$ is methoxy, followed by removal of the t-butoxycarbonyl protecting group. Of course, where final products are desired having $R_{10}$ as

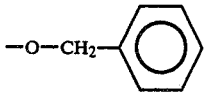

then the benzyl group is not removed from the intermediate of formula XVII.

When q is one, then the acid of formula XVIII is treated with the amino acid of the formula

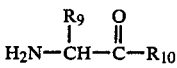

in the presence of a coupling reagent such as dicyclohexylcarbodiimide to give

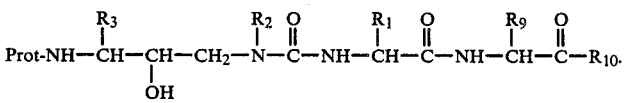   (XX)

Removal of the t-butoxycarbonyl amino protecting group as described above gives the alcohol of formula II.

The alcohol starting compound of XV can be prepared by treating the ketone of the formula

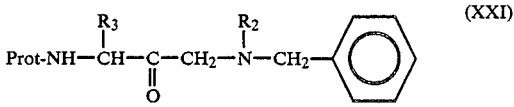   (XXI)

with a conventional reducing agent such as sodium borohydride followed by hydrogenation using palladium hydroxide on carbon catalyst.

The ketone of formula XXI can be prepared by treating the ketone of the formula

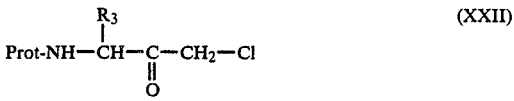   (XXII)

with an amine of the formula

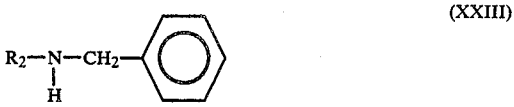   (XXIII)

in the presence of sodium iodide and sodium bicarbonate in a solvent such as dimethylformamide. When $R_2$ is hydrogen, the ketone of formula XXII is reacted with dibenzylamine. After reduction to the alcohol, both benzyl groups are removed by hydrogenation.

In the above reactions, if any of $R_1$, $R_2$, $R_3$, $R_4$, $R_5$, and $R_9$ are —$(CH_2)_n$-aryl wherein aryl is phenyl, 1-naphthyl, 2-naphthyl substituted with one or more hydroxy or amino groups, —$(CH_2)_n$-heterocyclo wherein heterocyclo is an imidazolyl, —$(CH_2)_n$—$NH_2$, —$(CH_2)_n$—SH, —$(CH_2)_n$—OH, or

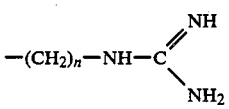

then the hydroxyl, amino, imiadazolyl, mercaptan, or guanidinyl function should should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The various peptide intermediates employed in an above procedure are known in the literature or can be readily prepared by known methods. See for example, The Peptides, Volume 1, "Major Methods of Peptide Bond Formation", Academic Press (1979).

Preferred compounds of this invention are those of formula I wherein:

X is

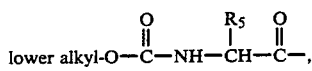

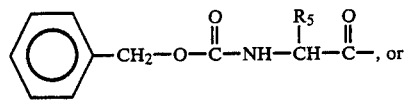

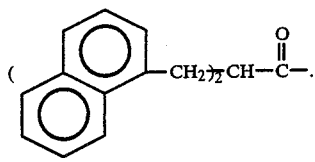

$R_1$ is lower alkyl of 3 to 5 carbons —$(CH_2)_n$-cyclopentyl, —$(CH_2)_n$-cyclohexyl,

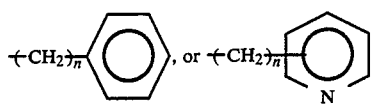

wherein n is an integer from 1 to 3.

$R_2$ is hydrogen, lower alkyl of 3 to 5 carbons, —$(CH_2)_m$-cyclopentyl, —$(CH_2)_m$-cyclohexyl,

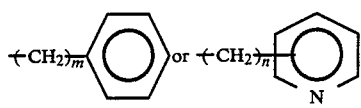

wherein m is an integer from 1 to 3 and n is also an integer from 1 to 3

$R_3$ is a lower alkyl of 3 to 5 carbons, —$(CH_2)_n$-cyclopentyl, —$(CH_2)_n$-cyclohexyl or

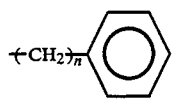

wherein n is an integer from 1 to 3.

$R_4$ is

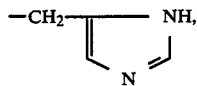

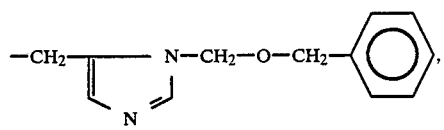

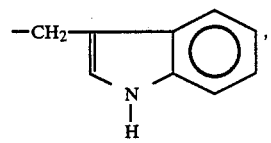

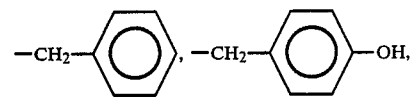

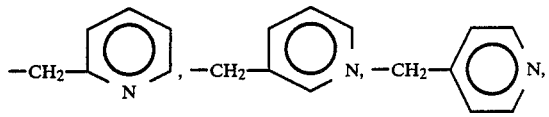

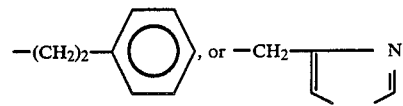

$R_5$ and $R_9$ are independently selected from

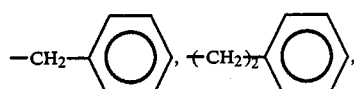

—$CH_2$—($\alpha$-naphthyl), —$CH_2$—($\beta$-naphthyl),

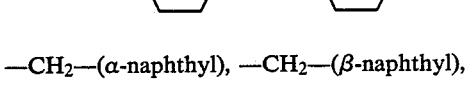

—$CH_2$-cyclopentyl, —$CH_2$-cyclohexyl,

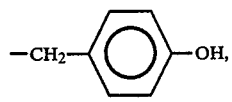

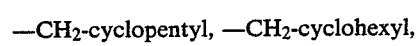

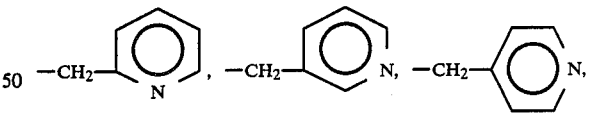

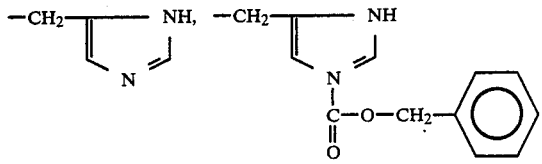

and 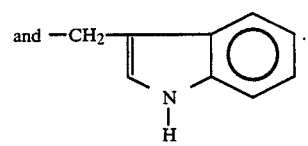

$R_{10}$ is —O—$CH_3$, —O—$C_2H_5$,

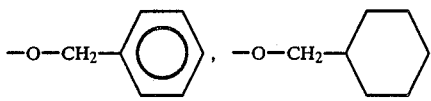

or hydroxy.

Most preferred are the above compounds wherein X is

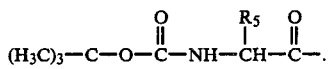

$R_1$ is

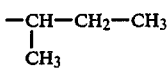

or $-CH-(CH_3)_2$, especially

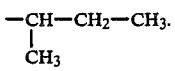

$R_2$ is hydrogen, $-CH_2-CH(CH_3)_2$, or $-CH(CH_3)_2$, especially hydrogen.

$R_5$ is

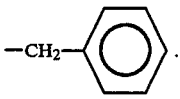

$R_4$ is

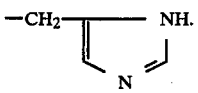

$R_3$ is $-CH_2-CH(CH_3)_2$.
q is zero or one, especially one.
$R_9$ is

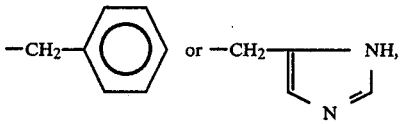

especially

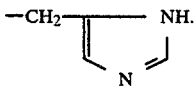

$R_{10}$ is $-O-CH_3$.

The compounds of formula I form salts with a variety of inorganic and organic acids. The nontoxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of $R_1$, $R_3$, $R_4$, $R_5$, and $R_9$ are other than hydrogen and at the carbon to which the —OH group is attached. Thus, the compounds of formula I can exist in diasteroisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are antihypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg., preferably about 250 to 500 mg. per kg. of body weight per day is appropriate to reduce blood pressure. The substance is preferably administered orally, but parenteral routes such as the subcutaneous, intramuscular, intraveneous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg., preferably about 3000 to 4000 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

N-[[[(3S)-3-[[N-[N-[(1,1-Dimethylethoxy)carbonyl]-L-phenylalanyl]-L-histidyl]amino]-2-hydroxy-5-methylhezyl](2-methylpropyl)amino]carbonyl]-L-valine, methyl ester, monohydrochloride (isomer A)

(a) (S)-[3-Methyl-1-[[(2-methylpropyl)(phenylmethyl)amino]acetyl]butyl]carbamic acid, 1,1dimethylethyl ester,4-methylbenzenesulfonic acid salt (1:1)

N-Methyl morpholine (16.5 ml., 150 mmole) is added to a stirred solution of N-[(1,1-dimethylethoxy)carbonyl]-L-leucine (34.67., 150 mmole) in dry tetrahydrofuran (135 ml.) at −15° followed by the dropwise addition of isobutyl chloroformate (19.5 ml., 150 mmole). After stirring at −15° for twenty minutes, it is filtered and diluted with ether (400 ml.) kept at −20°. This is added dropwise over 15 minutes to an ethereal solution of diazomethane (600 ml., generated from 60 g. of N-methyl-N'-nitro-N-nitrosoguanidine). After the addition is over the reaction is allowed to run at room temperature for two hours. Excess diazomethane is blown off by a stream of nitrogen. The ethereal solution is washed with saturated aqueous sodium bicarbonate and saturated sodium chloride solutions. The ethereal solution is concentrated in vacuo and the residue is dissolved in hexane. On cooling, 27.7 g. of (S)-[3-methyl-1-[(diazomethyl)carbonyl]butyl]carbamic acid, 1,1-dimethylethyl ester is obtained as a crystalline material; m.p. (88) 89°–90°.

Hydrochloric acid in acetic acid (2.2N, 94 mmole) is added dropwise to a stirred (ice-bath) solution of the above diazo product (24 g., 94 mmole) in ether (470 ml.). After stirring for 10 minutes the solution is evaporated in vacuo. The residue is dissolved in ethyl acetate:hexane (1:3) and passed through a small column of silica gel (400 g.) using ethyl acetate:hexane (1:3) for elution. A homogeneous material is obtained (23.2 g.). On crystallization from a mixture of ether and hexane fine crystalline (S)-[3-methyl-1-[(chloromethyl)carbonyl]butyl]carbamic acid, 1,1-dimethylethyl ester is obtained; m.p. 66°–68°.

A solution of (phenylmethyl)(2-methylpropyl)amine (8.16 g., 50 ml.), (S)-[3-methyl-1-[(chloromethyl)carbonyl]butyl]carbamic acid, 1,1-dimethylethyl ester (13.19 g., 50 mmole), sodium bicarbonate (6.3 g., 75 mmole), sodium iodide (3.74 g., 25 mmole) and dimethylformamide (100 ml.) is stirred at room temperature for 4 hours. It is then evaporated, taken into ethyl acetate and washed with water. The ethyl acetate solution is evaporated and the residue dissolved in ether. The ethereal solution is filtered to remove a very small amount of insoluble material. The ethereal solution is evaporated and the residue is chromatographed over a small column of silica gel (350 g.) using the solvent system ethyl acetate:hexane (1:4). The homogeneous fractions are pooled and evaporated. The residue (17.62 g.) is dissolved in ether and an ethyl acetate solution of p-toluenesulfonic acid (8.6 g., 45.2 mmole) is added. The crystallized salt is filtered to give 18.72 g. of (S)-[3-methyl-1-[[(2-methylpropyl) (phenylmethyl)amino]acetyl]butyl]carbamic acid, 1,1-dimethylethyl ester, 4-methylbenzenesulfonic acid salt (1:1); m.p. (140) 143°; $[\alpha]_D = -38.9°$ (c=2.2, methanol). TLC (silica gel; n-propanol: NH$_4$OH, 98:2) R$_f$=0.8.

Anal. calc'd. for $C_{30}H_{46}N_2O_6S \cdot C_7H_8O_3S$: C, 64.03; H, 8.24; N, 4.98; S, 5.70. Found: C, 63.83; H, 8.00; N, 4.97; S, 5.78.

(b) (S)-[1-[(RS)-1-Hydroxy-2-[(2-methylpropyl) (phenylmethyl)amino]ethyl]-3-methylbutyl]carbamic acid, 1,1-dimethylethyl ester, monohydrochloride.

The 4-methylbenzenesulfonic acid salt product from part (b) (5.62 g., 10 mmole) is taken into ethyl acetate and shook with saturated sodium bicarbonate solution. The ethyl acetate layer is dried over magnesium sulfate and evaporated in vacuo. The resulting free base (3.9 g.) is dissolved in ethanol (35 ml.). Sodium borohydride (400 mg., 10.4 mmole) is added to the stirring ethanolic solution at room temperature. After one hour the solution is evaporated and the residue is suspended in ethyl acetate and water and acidified to pH 2.0 using dilute hydrochloric acid. Then saturated sodium bicarbonate solution is added until the ethyl acetate solution is slightly basic. The ethyl acetate layer is dried over magnesium sulfate and evaporated to give 3.91 g. of alcohol product. An analytical sample of this alcohol is prepared as the hydrochloride salt as follows. Hydrochloric acid in dioxan solution (5N, 0.28 ml.) is added to an ethereal solution of an aliquot of the above alcohol (0.559 g., 1.42 mmole). The solution is concentrated and dried in high vacuum to give (S)-[1-[(RS)-1-hydroxy-2-[(2-methylpropyl)(phenylmethyl)amino]ethyl]-3-methylbutyl]carbamic acid, 1,1-dimethylethyl ester, monohydrochloride as a crisp solid; m.p. 50°–65°; $[\alpha]_D = -29.8°$ (c =1.54, methanol). TLC (silica gel, ethyl acetate:hexane, 1:4) R$_f$=0.47.

Anal. calc'd. for $C_{23}H_{40}N_2O_3 \cdot HCl \cdot 0.44 H_2O$: C, 63.21; H, 9.68; N, 6.41; Cl, 8.11. Found: C, 63.21; H, 9.49; N, 6.05; Cl, 7.88.

(c) (S)-[1-[(RS)-1-Hydroxy-2-[(2-methylpropyl)amino]ethyl]-3-methylbutyl]carbamic acid,1,1-dimethylethyl ester, monohydrochloride.

The alcohol product from part (b) (1.67 g., 4.25 mmole) is dissolved in methanol (50 ml.) and aqueous hydrochloric acid (1N, 4.25 ml.) is added. The solution is stirred under an atmosphere of hydrogen in the presence of palladium hydroxide on carbon catalyst (0.36 g.) for two hours. It is filtered through hyflo and concentrated to dryness in vacuo to give 1.31 g. of (S)-[1-[(RS)-1-hydroxy-2-[(2-methylpropyl)amino]ethyl]-3-methylbutyl]carbamic acid, 1,1-dimethylethyl ester, monohydrochloride; m.p. 138°–150°; $[\alpha]_D^{22} = -29.0°$ (c=1.2, methanol). TLC (silica gel; chloroform:methanol: acetic acid, 9:1:1) R$_f$=0.73.

Anal. calc'd. for $C_{16}H_{34}N_2O_3 \cdot HCl \cdot 0.2 H_2O$: C, 56.21; H, 10.41; N, 8.20; Cl, 10.37. Found: C, 56.21; H, 10.41; N, 8.14; Cl, 10.41.

(d) N-[[[(3S)-3-[[(1,1-Dimethylethoxy)carbonyl]amino]-2-hydroxy-5-methylhexyl](2-methylpropyl)amino]carbonyl]-L-valine, phenylmethyl ester L-Valine, phenylmethyl ester, benzene sulfonic acid salt (8.38 g., 23 mmole) is dissolved in methylene chloride (100 ml.) and the solution is cooled to −30°. N-Methyl morpholine (6.33 ml., 57.5 mmole) is added followed by a solution of phosgene in benzene (12.5% solution, 27.4ml., 34.5 mmole). The reaction mixture is stirred at −20° for 30 minutes. It is then evaporated in vacuo. A suspension of (S)-1-[1-hydroxy-2-[(2-methylpropyl) amino]ethyl]-3-methylbutyl]carbamic acid, 1,1-dimethylethyl ester, monohydrochloride (8.0 g., 23.6 mmole) in methylene chloride (50 ml.) and N-methyl morpholine (5.05 g., 46 mmole) are added to the above residue. The reaction mixture is stirred in an ice-bath for 2 hours and then at room temperature overnight. It is evaporated and the residue is taken into ethyl acetate and washed with water, saturated sodium bicarbonate solution, and 10% potassium hydrogen sulfate solution. The ethyl acetate extract is dried and evaporated. The crude product is chromatographed over silica gel (500 g.) using the solvent system ethyl acetate:hexane (1:2) to give 7.7 g., of N-[[[(3S)-3-[[(1,1-dimethylethoxy)carbonyl]amino]-2-hydroxy-5-methylhexyl(2-methylpropyl)amino]carbonyl]-L-valine, phenylmethyl ester as a gummy solid; m.p. 40°–49°; $[\alpha]_D^{22} = -41.4°$ (c=1.5, methanol). TLC (silica gel; ethyl acetate:hexane, 1:2) $R_f = 0.37$.

Anal. calc'd. for $C_{29}H_{49}N_3O_6$: C, 65.01; H, 9.22; N, 7.84. Found: C, 64.64; H, 9.14; N, 7.91.

(e)
N-[[[(3S)-3-[[(1,1-Dimethylethoxy)carbonyl]amino]-2-hydroxy-5-methylhexyl](2-methylpropyl)amino]carbonyl]-L-valine, methyl ester(isomer A)

The phenylmethyl ester product from part (d) (2.2 g., 4.1 mmole) is dissolved in methanol (75 ml.) and stirred under an atmosphere of hydrogen in the presence of palladium hydroxide on carbon catalyst for 16 hours. The catalyst is filtered through hyflo and the methanolic solution is evaporated to give 1.8 g. of N-[[[(3S)-3-[[(1,1dimethylethoxy)carbonyl]amino]-2-hydroxy-5-methylhexyl](2-methylpropyl)amino]carbonyl]-L-valine.

N-[[[(3S)-3-[[(1,1-Dimethylethoxy)carbonyl]amino]-2-hydroxy-5-methylhexyl](2-methylpropyl)amino]carbonyl]-L-valine (3.0 g., 6.73 mmole) is dissolved in an ethereal solution of diazomethane generated from 2.67 g. (17.7 mmole) of N-methyl-N'-nitro-N-nitrosoguanidine reagent. After keeping the solution at room temperature for one hour it is evaporated. The crude methyl ester product is chromatographed over silica gel (300 g.) using the solvent system ethyl acetate:hexane(2:5).

The earlier fractions (36–68, each 35 ml. fractions) contain the faster moving isomer. They are pooled and evaporated to give 1.2 g. of N-[[[(3S)-3-[[(1,1-dimethylethoxy)carbonyl]amino]-2-hydroxy-5-methylhexyl](2-methylpropyl)amino]-3-[[(1,1-dimethylethoxy)carbonyl]amino] carbonyl]-L-valine, methyl ester (isomer A); m.p. 40°–49°; $[\alpha]_D^{22} = +7.2°$ (c=1.5, methanol).

Anal. calc'd. for $C_{23}H_{45}N_3O_6 \cdot 0.25H_2O$: C, 59.52; H, 9.88; N, 9.05. Found: C, 59.50; H, 9.78; N, 8.97.

(f)
N-[[[(3S)-3-Amino-2-hydroxy-5-methylhexyl]-(2-methylpropyl)amino]carbonyl]-L-valine, methyl ester, monohydrochloride (isomer A)

The methyl ester (isomer A) product from part (e) (0.4 g., 0.87 mmole) is dissolved in a solution of hydrochloric acid in dioxane (5 ml., 4.9N) and allowed to stand at room temperature for 40 minutes. It is then evaporated and reevaporated from methanol and ether. The residue is dissolved in water, millipore filtered, and lyophilized to give 0.29 g. of N-[[[(3S)-3-amino-2-hydroxy-5-methylhexyl](2-methylpropyl)amino]-carbonyl]-L-valine, methyl ester, monohydrochloride (isomer A); m.p. 41°–61°; $[\alpha]^{22} = -2.94°$ (c=1, methanol). TLC (silica gel; chloroform:methanol:acetic acid, 8:1:1) $R_f = 0.61$.

Anal. calc'd. for $C_{18}H_{37}N_3O_4 \cdot HCl \cdot 0.7H_2O$: C, 52.88; H, 9.72; N, 10.28; Cl, 8.67. Found: C, 52.88; H, 9.42; N, 10.38; Cl, 8.41.

(g)
N-[N-[(1,1-Dimethylethoxy)carbonyl]-L-phenylalanyl]-1'-(phenylmethoxy)methyl]-L-histidine Thionyl chloride (27.2 ml., 375 mmole) is added in drops to a stirred solution in an ice-bath of L-histidine (38.75 g., 240 mmole) in methanol (500 ml.). After 15 minutes the ice-bath is removed and the reaction mixture is stirred at room temperature for one hour. After refluxing for 48 hours, it is concentrated in vacuo. The separated crystals are filtered using methanol for washings to give 48.93 g. of L-histidine, methyl ester, dihydrochloride. The methanolic solution on dilution with ether affords an additional 10 g. of product; m.p. 208°–209°; $[\alpha]_D^{22} = +10.1°$ (c=1.8, water).

Triethylamine (28 ml., 200 ml.) and di-tertbutyl dicarbonate (48 g., 220 mmole) are added to a suspension of L-histidine, methyl ester (24.2 g., 100 mmole) in methanol (80 ml.). After 3.5 hours, the mixture is filtered and the methanolic solution is concentrated in vacuo. The residue is taken into chloroform and washed with 10% citric acid. The crude product on crystallization from isopropyl ether affords 23.1 g. of N,1'-bis[(1,1dimethylethoxy)carbonyl]-L-histidine, methyl ester; m.p. (62) 88°–95°; $[\alpha]_D^{22} = +25.4°$ (c=1.1, carbon tetrachloride).

Benzylchloromethyl ether (11.6 ml., 83.6 mmole) is added to a solution of N,1'-bis[(1,1-dimethylethoxy)carbonyl]-L-histidine, methyl ester (24.7 g., 66.9 mmole) in dry methylene chloride (156 ml.) and the reaction mixture is stirred at room temperature for 5 hours. After concentrating in vacuo and on dissolution in ethyl acetate 17.85 g. of N-[(1,1-dimethylethoxy)carbonyl]-1'-[(phenylmethoxy)methyl-L-histidine, methyl ester, monohydrochloride hydrochloride crystallizes out; m.p. (148°) 152°–153°; $[\alpha]^{22} = -19.5°$ (c=1.8, methanol). This methyl ester product is dissolved in hydrogen chloride in acetic acid solution (60 ml., 1.5N) and kept at room temperature for 15 minutes. It is then evaporated in vacuo and the residue is dissolved in hot isopropanol. After cooling, the separated crystals are filtered to yield 7.08 g. of 1-[(phenylmethoxy)methyl]-L-histidine, methyl ester, dihydrochloride; m.p. (170) 173°–174°.

1-[(Phenylmethoxy)methyl]-L-histidine, methyl ester, dihydrochloride (1.79 g., 4.94 mmole), 1-hydroxybenzotriazole (0.756 g., 4.94 mmole), and N-[(1,1-dimethylethoxy)carbonyl]-L-phenylalanine (1.31 g., 4.94 mmole) are dissolved in dimethylformamide (16 ml.). While stirring the above solution in an ice-bath, dicyclohexylcarbodiimide (1.02 g., 4.94 mmole) and N,N-diisopropylethylamine (1.72 ml., 10 mmole) are added. After 3 hours the ice-bath is removed and the reaction mixture is stirred at room temperature overnight. It is then concentrated to dryness and the residue is triturated with ethyl acetate. The separated urea is filtered off. The ethyl acetate solution is washed with saturated sodium bicarbonate and then it is evaporated. The residue upon crystallization from ethyl acetate gives 1.97 g. of N-[N-[(1,1dimethylethoxy)carbonyl]-L- phenylalanyl]-1'-[(phenylmethoxy)methyl]-L-histidine, methyl ester; m.p. (165) 166°–168°.

N-[N-[(1,1-Dimethylethoxy)carbonyl]-L-phenylalanyl]-1'-[(phenylmethoxy)methyl]-L-histidine, methyl ester (4.5 g., 8.4 mmole) is dissolved in hot methanol (25 ml.). After cooling to room temperature aqueous sodium hydroxide solution (9.24 ml., 1N) is added and the mixture is stirred at room temperature for 3 hours. It is then concentrated in vacuo and water (60 ml.) is added to the residue. After cooling the aqueous solution in an ice-bath, it is acidified to pH 4.5 using aqueous hydrochloric acid. It is then extracted with ethyl acetate to yield 3.95 g. of crystalline N-[N-[(1,1-dimethylethoxy)carbonyl-L-phenylalanyl]-1'-[(phenylmethoxy)methyl]-L-histidine; m.p. 193°–194°; $[\alpha]_D^{22} = -4.8°$ (c=1.1, dimethylformamide).

(h)
N-[[[(3S)-3-[[N-[N-[(1,1-Dimethylethoxy)carbonyl]-L-phenylalanyl]-1'-[(phenylmethoxy)methyl]-L-histidinyl]amino]-2-hydroxy-5-methylhexyl](2-methylpropyl)amino]carbonyl]-L-valine, methyl ester (isomer A)

N-[[[(3S)-3-Amino-2-hydroxy-5-methylhexyl]-(2-methylpropyl)amino]carbonyl]-L-valine, methyl ester, monohydrochloride (isomer A) (0.396 g., 1 mmole), N-[N-[(1,1-dimethylethoxy)carbonyl]-L-phenylalanyl]-1'-[(phenylmethoxy)methyl-L-histidine (0.522 g., 1 mmole) and 1-hydroxybenzotriazole hydrate (0.153 g., 1 mmole) are dissolved in dimethylformamide (6 ml.). Diisopropylethyl amine (0.21 ml., 1.3 mmole) is added and the solution is cooled to −10°. While stirring under a gentle flow of nitrogen, dicyclohexylcarbodiimide (0.206 g., 1 mmole) is added. After stirring for one hour between −10° and 0°, the reaction mixture is then stirred in an ice-bath for 2 hours and then stirring is continued at ambient temperature overnight. The separated dicyclohexyl urea is filtered off and the dimethylformamide solution is evaporated. The residue is taken into ethyl acetate and washed with saturated sodium bicarbonate solution. The ethyl acetate extract after concentration is chromatographed over silica gel (45 g.) using the solvent system chloroform:methanol:acetic acid (9:0.5:0.5). Homogeneous fractions containing the product are pooled, evaporated, and the residue taken into ethyl acetate and washed with saturated sodium bicarbonate. The ethyl acetate extract is dried and evaporated to give 0.61 g. of N-[[[(3S)-3-[[N-[N-[(1,1-dimethylethoxy)carbonyl]-L-phenylalanyl]-1'-[(phenylmethoxy)methyl]-L-histidyl]-amino]-2-hydroxy-5-methylhexyl](2-methylpropyl)amino]carbonyl]-L-valine, methyl ester (isomer A).

(i)
N-[[[(3S)-3-[[N-[N-[(1,1-Dimethylethoxy)carbonyl]-L-phenylalanyl]-L-histidyl]amino]-2-hydroxy-5-methylhexyl](2-methylpropyl)amino]carbonyl]-L-valine, methyl ester, monohydrochloride (isomer A)

The methyl ester product from part (h) (0.3 g., 0.35 mmole) is dissolved in methanol (25 ml.). Aqueous hydrochloric acid (1N, 0.35 ml.) is added and the solution is stirred under an atmosphere of hydrogen in the presence of palladium hydroxide on carbon catalyst (0.1 g.) for 15 hours. It is then filtered through hyflo and evaporated to dryness. The residue is triturated with ether and filtered to give 0.22 g. of N-[[[(3S)-3-[[N-[N-[(1,1-dimethylethoxy)carbonyl]-L-phenylalanyl]-L-histidyl]amino]-2-hydroxy-5-methylhexyl](2-methylpropyl)amino]carbonyl]-L-valine, methyl ester, monohydrochloride (isomer A); m.p. 125°–137°; $[\alpha]_D^{22} = -2.9°$ (c=1, methanol). TLC (silica gel, chloroform:methanol:acetic acid, 15:1:1) $R_f = 0.23$.

Anal. calc'd. for $C_{38}H_{61}N_7O_8 \cdot HCl \cdot 1.1H_2O$: C, 57.02; H, 8.06; N, 12.25; Cl, 4.43. Found: C, 57.02; H, 7.89; N, 12.12; Cl, 4.99

EXAMPLE 2

N-[[[(3S)-3-[[N-[N-[(1,1-Dimethylethoxy)carbonyl]-L-phenylalanyl]-L-histidyl]amino]-2-hydroxy-5-methylhexyl](2-methylpropyl)amino]carbonyl]-L-valine, methyl ester, monohydrochloride (isomer B)

(a)
N-[[[(3S)-3-[[(1,1-Dimethylethoxy)carbonyl]amino]-2-hydroxy-5-methylhexyl](2-methylpropyl)amino]carbonyl]-L-valine, methyl ester (isomer B)

Following the chromatographic procedure described in Example 1 (e), fractions 70–90 (50 ml. fractions) contain the slow moving isomer. These fractions are pooled and evaporated to give 1.25 g. of N-[[[(3S)-3-[[(1,1-dimethylethoxy)carbonyl]amino]-2-hydroxy-5-methylhexyl](2-methylpropyl)amino]carbonyl]-L-valine, methyl ester (isomer B); m.p. 44°–55°; $[\alpha]_D^{22} = -78°$ (c=1, methanol). TLC (silica gel; ethyl acetate: hexane 1:1) $R_f = 0.38$.

Anal. calc'd. for $C_{23}H_{45}N_3O_6$: C, 60.10; H, 9.87; N, 9.14; Found: C, 59.84; H, 9.82; N, 9.00.

(b)
N-[[[(3S)-3-Amino-2-hydroxy-5-methylhexyl]-(2-methylpropyl)amino]carbonyl]-L-valine, methyl ester, monohydrochloride (isomer B)

The methyl ester (isomer B) product from part (a) (0.35 g., 0.76 mmole) is dissolved in a solution of hydrochoric acid in dioxane (4 ml., 4.9N) and allowed to stand at room temperature for 50 minutes. It is then evaporated and reevaporated from methanol and ether. The crude residue is dissolved in water, millipore filtered, and lyophilized to give 0.27 g. of N-[[[(3S)-3-amino-2-hydroxy-5-methylhexyl](2-methylpropyl)amino]carbonyl]-L-valine, methyl ester, monohydrochloride (isomer B).

(c)
N-[[[(3S)-3-[[N-[N-[(1,1-Dimethylethoxy)carbonyl]-L-phenylalanyl]-1'-[(phenylmethoxy)methyl]-L-histidyl]amino]-2-hydroxy-5-methylhexyl]-(2-methylpropyl)amino]carbonyl]-L-valine, methyl ester (isomer A)

N-[[[(3S)-3-Amino-2-hydroxy-5-methylhexyl](2-methylpropyl)amino]carbonyl]-L-valine, methyl ester, monohydrochloride (isomer B) (0.36 g., 0.91 mmole), N-[N-[(1,1-dimethylethoxy)carbonyl]-L-phenylalanyl]-1'-[(phenylmethoxy)methyl]-L-histidine (0.475 g., 0.91 mmole) and 1-hydroxybenzotriazole hydrate (0.139 g., 0.91 mmole) are dissolved in dimethylformamide (6.5 ml.). Diisopropylethylamine (0.21 ml., 1.3 mmole) is added and the solution is stirred in an ice-bath. Dicyclohexylcarbodiimide (0.188 g., 0.91 mmole) is added and the stirring of the reaction mixture is continued at ambient temperature overnight. Dicyclohexylurea is filtered off and the dimethylformamide solution is evaporated. The residue is taken into ethyl acetate and washed with saturated sodium bicarbonate solution. The ethyl acetate extract after concentration is chromatographed over silica gel (50 g.) using the solvent system chloroform:methanol:acetic acid, 10:0.5:0.5. Homogeneous fractions containing the product are pooled, evaporated, and the residue taken into ethyl acetate and washed with saturated sodium bicarbonate. The ethyl acetate extract is dried and evaporated to give 0.62 g. of N-[[[(3S)-3-[[N-[N-[(1,1-dimethylethoxy)carbonyl-L-phenylalanyl]-1'-[(phenylmethoxy)methyl]-L-histidyl]amino]-2-hydroxy-5-methylhexyl](2-methoxypropyl)amino]carbonyl]-L-valine, methyl ester (isomer A).

(d)
N-[[[(3S)-3-[[N-[N-[(1,1-Dimethylethoxy)carbonyl]-L-phenylalanyl]-L-histidyl]amino]-2-hydroxy-5-methylhexyl](2-methylpropyl)amino]carbonyl]-L-valine, methyl ester, monohydrochloride (isomer B)

The methyl ester (isomer B) product from part (c) (0.32 g., 0.37 mmole) is dissolved in methanol (25 ml.). Aqueous hydrochloric acid (1N, 0.37 mmole) is added and the solution is stirred under an atmosphere of hydrogen in the presence of palladium hydroxide on carbon catalyst (0.1 g.) for 18 hours. It is then filtered through hyflo and evaporated to dryness. The residue is dissolved in isopropanol (3 ml.) and while shaking vigorously isopropyl ether (35 ml.) is added. The resulting precipitate is filtered and dried to give 0.184 g. of N-[[[(3S)-3-[[N-[N-[(1,1-dimethylethoxy)carbonyl]-L-phenylalanyl]-L-histidyl]amino]-2-hydroxy-5-methylhexyl](2-methylpropyl)amino]carbonyl]-L-valine, methyl ester monohydrochloride (isomer B); m.p. 115°–140°; $[\alpha]_D^{22} = -36.9°$ (c=1.1, methanol). TLC (silica gel; chloroform:methanol:acetic acid, 15:1:1) $R_f=0.20$.

Anal. calc'd. for $C_{38}H_{61}N_7O_8 \cdot HCl \cdot 1.34H_2O$: C, 56.73; H, 8.10; N, 12.19; Cl, 4.41. Found: C, 56.73; H, 7.99; N, 12.28; Cl, 4.66.

EXAMPLE 3
N-[N-[[[(3S)-3-[[N-[N-[(1,1-Dimethylethoxy)carbonyl]-L-phenylalanyl]-L-histidyl]amino]-2-hydroxy-5-methylhexyl](2-methylpropyl)amino]carbonyl]-L-valyl]-L-phenylalanine, methyl ester, monohydrochloride (a)
N-[[[(3S)-3-[[(1,1-Dimethylethoxy)carbonyl]amino]-2-hydroxy-5-methylhexyl](2-methylpropyl)amino]carbonyl]-L-valine N-[[[(3S)-3-[[(1,1-Dimethylethoxy)carbonyl]amino]-2-hydroxy-5-mechylhexyl](2-methylpropyl)amino]carbonyl]-L-valine, phenylmethyl ester (2.0 g., 3.73 mmole), prepared as set forth in Example 1(d), is dissolved in methanol (100 ml.) and stirred under an atmosphere of hydrogen for 16 hours in the presence of palladium hydroxide on carbon catalyst (400 mg.). It is filtered and the methanolic solution is evaporated to give 1.66 g. of N-[[[(3S)-3-[[(1,1-dimethylethoxy)carbonyl]amino]-2-hydroxy-5-methylhexyl](2-methylpropyl)amino]carbonyl]-L-valine as a foamy solid.

(b)
N-[N-[[[(3S)-3-[[(1,1-Dimethylethoxy)carbonyl]amino]-2-hydroxy-5-methylhexyl](2-methylpropyl)amino]carbonyl]-L-valyl]-L-phenylalanine, methyl ester N-[[[(3S)-3-[[(1,1-Dimethylethoxy)carbonyl]amino]-2-hydroxy-5-methylhexyl](2-methylpropyl)amino]carbonyl]-L-valine (1.62 g., 3.63 mmole), L-phenylalanine, methyl ester, monohydrochloride (0.94 g., 4.36 mmole) and N-hydroxy succinimide (0.42 g., 3.63 mmole) are dissolved in dimethylformamide (13 ml.). While stirring the above solution in an ice-bath, dicyclohexylcarbodiimide (0.75 g., 3.63 mmole) and diisopropylethyl amine (0.85 ml. 5.3 mmole) are added. The reaction is continued in the ice-bath for two hours and then at ambient temperture overnight. It is filtered and the dimethylformamide solution is evaporated in vacuo. The residue is taken into ethyl acetate and washed with saturated sodium bicarbonate, water, and aqueous hydrochloric acid (0.25N) solutions. The ethyl acetate solution is dried and then evaporated. The crude product is chromatographed over silica gel (100 g.) eluting with ethyl acetate:hexane (1:1) to give 1.4 g. of N-[N-[[[(3S)-3-[[(1,1-dimethylethoxy)carbonyl]amino]-2-hydroxy-5-methylhexyl](2-methylpropyl)amino]carbonyl]-L-valyl]-L-phenylalanine, methyl ester; m.p. (52) 63°–74°; $[\alpha]_D^{22} = -26.4°$ (c=1.2, methanol). TLC (silica gel, ethyl acetate:hexane, 4:6) $R_f=0.4$ and 0.44.

Anal. calc'd. for $C_{32}H_{54}N_4O_7$: C, 63.34; H, 8.97; N, 9.23. Found: C, 63.04; H, 8.87; N, 9.17.

(c)
N-[N-[[[(3S)-3-Amino-2-hydroxy-5-methylhexyl]-(2-methylpropyl)amino]carbonyl]-L-valyl]-L-phenylalanine, methyl ester, monohydrochloride The methyl ester product from part (b) (0.92 g., 1.502 mmole) is dissolved in a solution of hydrochloric acid in dioxane (4.9N, 8 ml.). After keeping the solution at room temperature for 45 minutes it is evaporated. The residue is chromatographed over silica gel (100 g.) eluting with chloroform:methanol:acetic acid (12:0.9:0.9). Fractions containing homogeneous material are pooled and evaporated (0.49 g.). The impure fractions are pooled, evaporated and rechromatographed over silica gel (20 g.) eluting with the solvent system chloroform:methanol:acetic acid (12:1:1) to give an additional amount (0.15 g.) of product resulting in a total yield of 0.64 g. of N-[N-[[[(3S)-3-amino-2-hydroxy-5-methylhexyl](2-methylpropyl)amino]carbonyl]-L-valyl]-L-phenylalanine, methyl ester, monohydrochloride.

(d)
N-[N-[[[(3S)-3-[[N-[N-[(1,1-Dimethylethoxy)carbonyl]-L-phenylalanyl]-1'-[(phenylmethoxy)methyl]-L-histidyl]amino]-2-hydroxy-5-methylhexyl](2-methylpropyl)amino]carbonyl]-L-valyl]-L-phenylalanine, methyl ester N-[N-[[[(3S)-3-Amino-2-hydroxy-5-methylhexyl]-(2-methylpropyl)amino]carbonyl]-L-valyl]-L-phenylalanine, methyl ester, monohydrochloride (0.32 g., 0.59 mmole), N-[N-[1,1-dimethylethoxy)carbonyl]-L-phenylalanyl]-1'-[(phenylmethoxy)methyl]-L-histidine (0.309 g., 0.59 mmole), and 1-hydroxybenzotriazole hydrate (0.091 g., 0.59 mmole) are dissolved in dimethylformamide (3 ml.). A small amount of benzene (3 ml.) is used for the washings and then it is evaporated off. While stirring the above solution at −10° under a gentle flow of nitrogen, dicyclohexylcarbodiimide (0.122 g., 0.59 mmole) and diisopropylethylamine (0.145 ml., 0.9 mmole) are added. After stirring at −10° for two hours, it is then stirred in an ice-bath for one hour, and stirring is then continued at ambient temperature overnight. The reaction mixture is then evaporated, diluted with ethyl acetate, and filtered to remove dicyclohexyl urea. The ethyl acetate solution is washed with saturated sodium bicarbonate and water and then evaporated. The residue is chromatographed over silica gel (35 g.) eluting with the solvent system chloroform:methanol:acetic acid (10:0.5:0.5). The fractions containing the desired product are pooled, evaporated, and the residue is dissolved in ethyl acetate and washed with saturated sodium bicarbonate solution. The ethyl acetate solution is then evaporated to give 0.48 g. of N-[N-[[[(3S)-3-[[N-[N-[(1,1-dimethylethoxy)carbonyl]-L-phenylal -1'-[(phenylmethoxy)methyl]-L-histidyl]amino]-2-hydroxy-5-methylhexyl](2-methylpropyl)amino]carbonyl]-L-valyl]-L-phenylalanine, methyl ester.

(e) N-[N-[[[(3S)-3-[[N-[N-[(1,1-Dimethylethoxy)carbonyl]-L-phenylalanyl]-L-histidyl]amino]-2-hydroxy-5-methylhexyl](2-methylpropyl)amino]carbonyl]-L-valyl]-L-phenylalanine, methyl ester, monohydrochloride The methyl ester product from part (d) (0.195 g., 0.193 mmole) is dissolved in methanol (25 ml.). Aqueous hydrochloric acid (1N, 0.2 ml.) is added and the solution is stirred under an atmosphere of hydrogen in the presence of palladium hydroxide on carbon catalyst (0.1 g.) for 18 hours. It is then filtered through hyflo and evaporated to dryness. The residue (0.16 g.) is stirred with ether and filtered. The solid (0.145 g.) is dissolved in isopropanol (0.5 ml.) and diluted with isopropyl ether (35 ml.). This sample (120 mg.) is again precipitated from isopropanol-isopropyl ether to give 105 mg. of N-[N-[[[(3S)-3-[[N-[N-[(1,1-dimethylethoxy)carbonyl]-2-phenylalanyl]-L-histidyl]amino]-2-hydroxy-5-methylhexyl](2-methylpropyl)amino]carbonyl]-L-valyl]-L-phenylalanine, methyl ester, monohydrochloride; m.p. (129) 135°-145°; $[\alpha]_D^{22} = -13.5°$ (c=1, methanol). TLC (silica gel; chloroform:methanol:acetic acid, 15:1:1) $R_f=0.31$.

Anal. calc'd. for $C_{47}H_{70}N_8O_9 \cdot HCl \cdot 2.42H_2O$: C, 58.12; H, 7.87; N, 11.54; Cl, 3.65. Found: C, 58.12; H, 7.60; N, 11.50; Cl, 4.76.

EXAMPLE 4
N-[N-[[[(3S)-3-[[N-[N-[(1,1-Dimethylethoxy)carbonyl]-L-phenylalanyl]-L-histidinyl]amino]-2-hydroxy-5-methylhexyl](1-methylethyl)amino]carbonyl]-L-isoleucyl]-L-histidine, methylester, dihydrochloride (a) (S)-[3-Methyl-1-[[(1-methylethyl)(phenylmethyl)amino]acetyl]butyl]carbamic acid, 1,1-dimethylethyl ester A solution of (S)-[3-methyl-1-[(chloromethyl)carbonyl]butyl]carbamic acid, 1,1-dimethylethyl ester (6.6 g., 25 mmole), N-isopropylbenzylamine (4.182 ml., 25 mmole), sodium bicarbonate (3.15 g., 37.5 mmole), sodium iodide (1.875 g., 12.5 mmole), and dimethylformamide (80 ml.) are stirred at room temperature for 7.5 hours. The reaction mixture is then evaporated in vacuo and the residue is taken into ethyl acetate and washed with water to give 9.4 g. of (S)-[3-methyl-1-[[(1-methylethyl)(phenylmethyl)amino]acetyl]butyl]carbamic acid, 1,1-dimethylethyl ester.

(b) (3S)-[1-[(R,S)-1-Hydroxy-2-[(1methylethyl)(phenylmethyl)amino]ethyl]-3-methylbutyl]carbamic acid,1,1-dimethylethyl ester Sodium borohydride (1 g., 26.3 mmole) is added to a solution of (S)-[3-methyl-1-[[(1methylethyl)(phenylmethyl)amino]acetyl]butyl]carbamic acid, 1,1-dimethylethyl ester (9.4 g., 25 mmole) in ethanol (75 ml.). The solution is stirred at room temperture for one hour. It is then concentrated to dryness in vacuo. The residue is suspended in ethyl acetate/water and acidified to pH 2.0 by adding dilute hydrochloric acid. The aqueous layer is then made basic by adding saturated sodium bicarbonate. The aqueous layer is then extracted with ethyl acetate. The ethyl acetate solution on evaporation and redissolution in a mixture of ethyl acetate:hexane (1:3) deposits 2.526 g. of a crystalline material which is found to be one of the isomeric alcohols. The mother liquor is then chromatographed over silica gel (300 g.) using the solvent system ethyl acetate:hexane (1:3). The purified isomeric alcohol derivatives are pooled to give 7.0 g. of (3S)-[1-[(R,S)-1-hydroxy-2-[(1methylethyl)(phenylmethyl)amino]ethyl]-3-methylbutyl]carbamic acid, 1,1-dimethylethyl ester.

(c) (3S)-[1-[(R,S)-1-Hydroxy-2-[(1methylethyl)amino]ethyl]-3-methylbutyl]carbamic acid, 1,1-dimethylethyl ester, monohydrochloride A solution of the carbamic acid, 1,1dimethylethyl ester product from part (b) (2.27 g., 6 mmole) in methanol (40 ml.) and aqueous hydrochloric acid (1N, 6 ml.) is stirred under an atmosphere of hydrogen in the presence of palladium hydroxide on carbon catalyst (460 mg.) for 3.5 hours. The mixture is then filtered through hyflo and evaporated to give 1.87 g. of (3S)-[1-[(R,S)-1-hydroxy-2-[(1-methylethyl)amino]ethyl]-3-methylbutyl]carbamic acid, 1,1-dimethylethyl ester, monohydrochloride.

(d) N-[[[(3S)-3-[[(1,1-Dimethylethoxy)carbonyl]amino]-2-hydroxy-5-methylhexyl](1-methylethyl)amino]carbonyl]-L-isoleucine, phenylmethyl ester N-Methylmorpholine (0.74 ml., 6.7 mmole) is added to a stirred solution of L-isoleucine, phenylmethyl ester, hydrochloride (1.06 g., 2.7 mmole) in methylene chloride (12 ml.) at −30° followed by the dropwise addition of a solution of phosgene in benzene (12.5%, 3.2 ml., 4.032 mmole). After stirring for 30 minutes at −20°, the mixture is concentrated to dryness in vacuo. A solution of (3S)-[1-[(R,S)-1-hydroxy-2-[(1methylethyl)amino]ethyl]-3-methylbutyl]carbamic acid, 1,1-dimethylethyl ester, monohydrochloride (0.9 g., 2.77 mmole) in methylene chloride (6 ml.) is added to the above residue. While stirring the above solution in an ice-bath, N-methylmorpholine (0.59 ml., 5.36 mmole) is added and the stirring is continued for 2 hours in the ice-bath and then overnight at room temperature. The reaction mixture is then evaporated to dryness, the residue is taken up in ethyl acetate and washed neutral with saturated sodium bicarbonate and 10% potassium bisulfate. The ethyl acetate extract after drying is chromatographed (silica gel, 75 g.) using the solvent system ethyl acetate:hexane (1:1) to give 0.78 g. of N-[[[(3S)-3-[[(1,1-dimethylethoxy)carbonyl]amino]-2-hydroxy-5-methylhexyl](1-methylethyl)amino]carbonyl]-L-isoleucine, phenylmethyl ester.

(e) N-[[[(3S)-3-[[(1,1-Dimethylethoxy)carbonyl]amino]-2-hydroxy-5-methylhexyl](1methylethyl)amino]carbonyl]-L-isoleucine A solution of the phenylmethyl ester product from part (d) (0.78 g., 1.45 mmole) in methanol (40 ml.) is stirred under an atmosphere of hydrogen overnight in the presence of palladium hydroxide on carbon catalyst (0.15 g.). The mixture is then filtered through hyflo and concentrated to dryness to give 0.6 g. of N-[[[(3S)-3-[[(1,1-dimethylethoxy)carbonyl]amino]-2-hydroxy-5-methylhexyl](1methylethyl)amino]carbonyl]-L-isoleucine.

(f)
N-[N-[[[(3S)-3-[[(1,1-Dimethylethoxy)carbonyl]amino]-2-hydroxy-5-methylhexyl](1methylethyl)amino]carbonyl]-L-isoleucyl]-1'-[(phenylmethoxy)methyl]-L-histidine, methyl ester Dicyclohexylcarbodiimide (0.277 g., 1.35 mmole) is added to a stirred (ice-bath) mixture of the L-isoleucine product from part (e) (0.6 g., 1.35 mmole), N-hydroxy succinimide (0.155 g., 1.35 mmole), 1'-[(phenylmethoxy)methyl]-L-histidine, methyl ester, monohydrochloride (0.488 g., 1.35 mmole), diisopropylethylamine (0.47 ml., 2.76 mmole), and dimethylformamide (5 ml.). Stirring is continued at 5° (cold room) overnight. The reaction mixture is then evaporated and the residue is taken up in ethyl acetate. The separated dicyclohexyl urea is filtered off and then the ethyl acetate solution is washed with saturated sodium bicarbonate. After evaporation of the ethyl acetate extract, the residue is chromatographed (silica gel, 75 g.) using the solvent system ethyl acetate:methanol (9:1) to give 0.54 g. of N-[N-[[[(3S)-3-[[(1,1-dimethyl ethoxy)carbonyl]amino]-2-hydroxy-5-methylhexyl]-(1-methylethyl)amino]carbonyl]-L-isoleucyl]-1'-[(phenylmethoxy)methyl]-L-histidine, methyl ester.

(g)
N-[N-[[[(3S)-3-Amino-2-hydroxy-5-methylhexyl]-(1-methylethyl)amino]carbonyl]-L-isoleucyl]-1'-[(phenylmethoxy)methyl]-L-histidine, methyl ester, dihydrochloride The L-histidine, methyl ester product from part (f) (0.545 g., 0.76 mmole) is dissolved in a solution of hydrochloric acid in dioxane (2N, 12 ml.) and kept at room temperature for 3.5 hours. It is then concentrated to dryness in vacuo to give 0.53 g. of N-[N-[[[(3S)-3-amino-2-hydroxy-5-methylhexyl](1-methylethyl)amino]carbonyl]-L-isoleucyl-1'-[(phenylmethoxy)methyl]-L-histidine, methyl ester, dihydrochloride.

(h)
N-[N-[[[(3S)-3-[[N-[N-[(1,1-(Dimethylethoxy)carbonyl]-L-phenylalanyl]-1'-[(phenylmethoxy)methyl]-L-histidinyl]amino]-2-hydroxy-5-methylhexyl](1methylethyl)amino]carbonyl]-L-isoleucyl]-1'-[(phenylmethoxy)methyl]-L-histidine, methyl ester Dicyclohexylcarbodiimide (0.156 g., 0.76 mmole) is added to a stirred (ice-bath) solution of the L-histidine, methyl ester, dihydrochloride product from part (g) (0.53 g., 0.76 mmole), 1-hydroxybenzotriazole hydrate (0.116 g., 0.76 mmole), N-[N-[(1,1-dimethylethoxy)carbonyl]-L-phenylalanyl]-1'-[(phenylmethoxy)methyl]-L-histidine (0.396 g., 0.76 mmole), diisopropylethylamine (0.264 ml., 1.51 mmole) and dimethylformamide (4 ml.). Stirring is continued at 5° (cold room) overnight. The reaction mixture is then concentrated to dryness in vacuo. The residue is taken into ethyl acetate, separated dicyclohexyl urea is filtered off, and the ethyl acetate solution is washed with saturated sodium bicarbonate. The ethyl acetate solution after evaporation is chromatographed (silica gel, 75 g.) using the solvent system ethyl acetate:methanol (8.5:1.5) to give 0.48 g. of N-[N--[[[(3S)-3-[[N-[N-[(1,1-dimethylethoxy)carbonyl]-L-phenylalanyl]-1'-[(phenylmethoxy)methyl]-L-histidinyl]amino]-2-hydroxy-5-methylhexyl](1-methylethyl)amino]carbonyl]-L-isoleucyl]-1'-[(phenylmethoxy)methyl]-L-histidine, methyl ester.

(i)
N-[N-[[[(3S)-3-[[N-[N-[(1,1-Dimethylethoxy)carbonyl]-L-phenylalanyl]-L-histidinyl]amino]-2-hydroxy-5-methylhexyl](1-methylethyl)amino]carbonyl]-L-isoleucyl]-L-histidine, methyl ester, dihydrochloride The L-histidine, methyl ester product from part (h) (0.466 g., 0.415 mmole) is dissolved in methanol (25 ml.) and aqueous hydrochloric acid (1N, 0.79 ml.). The mixture is stirred under an atmosphere of hydrogen in the presence of palladium hydroxide on carbon catalyst (0.1 g.) for 48 hours. The solution is filtered through hyflo and concentrated to dryness in vacuo. The residue is chromatographed (silica gel, 39 g.) using the solvent system ethyl acetate:acetic acid:water (4:1:1). The fractions containing the product are pooled and evaporated. The residue is dissolved in methanol and aqueous hydrochloric acid (1N, 0.52 ml.) is added. The mixture is then evaporated, the residue is dissolved in a minimum amount of methanol, and passed through a column of LH-20 using methanol for elution to give 0.224 g. of product. 174 mg. of the above solid is dissolved in methanol and aqueous hydrochloric acid (1N, 0.047 ml.) is added and the solution is evaporated to dryness to give 0.171 g. of N-[N-[[[(3S)-3-[[N-[N-[(1,1-dimethylethoxy)carbonyl]-L-phenylalanyl]-L-histidinyl]amino]-2-hydroxy-5-methylhexyl(1methylethyl)amino]carbonyl]-L-isoleucyl]-L-histidine, methyl ester, dihydrochloride; m.p. (115) 148°-168°; $[\alpha]_D^{22} = -7.8°$ (c=1.2, methanol). TLC (silica gel; ethyl acetate:acetic acid:water, 4:1:1) $R_f=0.45$.

Anal. calc'd. for $C_{44}H_{68}O_9N_{10} \cdot 2HCl \cdot 2.5\ H_2O$: C, 52.90; H, 7.57; N, 14.02; Cl, 7.10. Found: C, 52.86; H, 7.24; N, 13.73; Cl, 6.97.

EXAMPLE 5

N-[[[(3S)-3-[[N-[N-[(1,1-Dimethylethoxy)carbonyl]-L-phenylalanyl]-L-histidiyl]amino]-2-hydroxy-5-methylhexyl](1-methylethyl)amino]carbonyl]-L-isoleucine, methyl ester, isomer A, monohydrochloride (a)
N-[[[(3S)-3-[[(1,1-Dimethylethoxy)carbonyl]amino]-2-hydroxy-5-methylhexyl(1-methylethyl)amino]carbonyl]-L-isoleucine, methyl ester, isomer A N-Methylmorpholine (0.79 ml., 7.1 mmole) is added to a stirred solution of L-isoleucine, methyl ester, monohydrochloride (0.442 g., 2.43 mmole) in methylene chloride (10 ml.) at −30° followed by the dropwise addition of a solution of phosgene in benzene (12.5%, 2.94 ml., 3.7 mmole). After stirring for 20 minutes at −20°, the mixture is concentrated to dryness in vacuo. An ice-cold solution of (3S)-[1-[(R,S)-1-hydroxy-2-[(1-methylethyl)amino]ethyl]-3-methylbutyl]carbamic acid, 1,1-dimethylethyl ester, monohydrochloride (0.79 g., 2.43 mmole) in methylene chloride (10 ml.) and N-methylmorpholine (0.54 ml., 4.86 mmole) is added to the above residue. The reaction mixture is stirred in an ice-bath for 6 hours and at room temperature overnight. It is then evaporated to dryness, the residue is taken up in ethyl acetate and washed with saturated sodium bicarbonate solution and 10% potassium bisulfate solution. The ethyl acetate extract after evaporation is chromatographed (silica gel, 125 g.) using the solvent system ethyl acetate:hexane (4:3). In this chromatography the two diastereoisomers are separated giving 0.26 g. of N-[[[(3S)-3-[[(1,1-dimethylethoxy)carbonyl]amino]-2-hydroxy-5-methylhexyl](1-methylethyl)amino]carbonyl]-L-isoleucine, methyl ester, isomer A and 0.448 g. of N-[[[(3S)-3-[[(1,1-dimethylethoxy)carbonyl]amino]-2-hydroxy-5-methylhexyl](1-methylethyl)amino]carbonyl]-L-isoleucine, methyl ester, isomer B.

(b)
N-[[[(3S)-3-Amino-2-hydroxy-5-methylhexyl]-(1-methylethyl)amino]carbonyl]-L-isoleucine, methyl ester, isomer A The L-isoleucine, methyl ester, isomer A product from part (a) (0.25 g., 0.544 mmole) is dissolved in a solution of hydrochloric acid in dioxane (2N, 2.25 ml.). After keeping the solution at room temperature for 4 hours, it is evaporated in vacuo to give N-[[[(3S)-3-amino-2-hydroxy-5-methylhexyl](1-methylethyl)amino]carbonyl]-L-isoleucine, methyl ester, isomer A.

(c)
N-[[[(3S)-3-[[N-[N-[(1,1-Dimethylethoxy)carbonyl]-L-phenylalanyl]-1'-[(phenylmethoxy)methyl]-L-histidyl]amino]-2-hydroxy-5-methylhexyl](1-methylethyl)amino]carbonyl]-L-isoleucine, methyl ester, isomer A Dicyclohexylcarbodiimide (0.109 g., 0.59 mmole) is added to a stirred (ice-bath) solution of N-[[[(3S)-3-amino-2-hydroxy-5-methylhexyl](1-methylethyl)amino]carbonyl]-L-isoleucine, methyl ester, isomer A from part (b), 1-hydroxybenzotriazole hydrate (0.081 g., 0.53 mmole), N-[N-[(1,1-dimethylethoxy)carbonyl]-L-phenylalanyl]-1'-[(phenylmethoxy)methyl]-L-histidine (0.277 g., 0.53 mmole), diisopropylethylamine (0.15 ml., 0.885 mmole), and dimethylformamide (3 ml.). Stirring is continued at 5° (cold room) overnight. It is then concentrated to dryness in vacuo and the residue is triturated with ethyl acetate and the separated dicyclohexyl urea is filtered off. The ethyl acetate solution is washed with saturated sodium bicarbonate solution and water. It is then evaporated in vacuo and the residue chromatographed (silica gel, 75 g.) using the solvent system chloroform:methanol:acetic acid (10:0.5:0.5). The product containing fractions are pooled, evaporated, and the residue is dissolved in ethyl acetate and washed with saturated sodium bicarbonate solution. The ethyl acetate solution is dried over magnesium sulfate and evaporated in vacuo to give 0.26 g. of N-[[[(3S)-3-[[N-[N-[(1,1-dimethylethoxy)carbonyl]-L-phenylalanyl]-1'-(phenylmethoxy)methyl]-L-histidinyl]amino]-2-hydroxy-5-methylhexyl](1-methylethyl)amino]carbonyl]-L-isoleucine, methyl ester, isomer A.

(d)
N-[[[(3S)-3-[[N-[N-[(1,1-Dimethylethoxy)carbonyl]-L-phenylalanyl]-L-histidyl]amino]-2-hydroxy-5-methylhexyl](1-methylethyl)amino]carbonyl]-L-isoleucine, methyl ester, isomer A, monohydrochloride The L-isoleucine, methyl ester, isomer A product from part (c) (0.237 g., 0.274 mmole) is dissolved in methanol (3 ml.). Hydrochloric acid (0.1N, 2.3 ml., prepared by diluting 1N aqueous hydrochloric acid with methanol) is added and the solution is stirred under an atmosphere of hydrogen in the presence of palladium hydroxide on carbon catalyst (65 mg.) for 18 hours. The mixture is then filtered through Celite and evaporated. The residue is stirred with isopropyl ether and filtered to give 0.165 g. of N-[[[(3S)-3-[[N-[N-[(1,1-dimethylethoxy)carbonyl]-L-phenylalanyl]-L-histidyl]amino]-2-hydroxy-5-methylhexyl]-(1-methylethyl)amino]carbonyl]-L-isoleucine, methyl ester, isomer A, monohydrochloride; m.p. 101°–116°; $[\alpha]_D^{20} = +11.65$ (c=1, methanol). TLC (silica gel; ethyl acetate:acetic acid:water, 12:1:1) $R_f = 0.28$.

Anal. calc'd. for C$_{38}$H$_{61}$N$_7$O$_8$ · HCl · 1.5H$_2$O: C, 56.52; H, 8.11; N, 12.14; Cl, 4.39. Found: C, 56.65; H, 8.00; N, 11.73; Cl, 4.48.

EXAMPLE 6

N-[[[(3S)-3-[[N-[N-[(1,1-Dimethylethoxy)carbonyl]-L-phenylalanyl]-L-histidyl]amino]-2-hydroxy-5-methylhexyl](1-methylethyl)amino]carbonyl]-L-isoleucine, methyl ester, isomer B, monohydrochloride

(a)
N-[[[(3S)-3-Amino-2-hydroxy-5-methylhexyl](1-methylethyl)amino]carbonyl]-L-isoleucine, methyl ester, isomer B The L-isoleucine, methyl ester, isomer B product from Example 5(a) (0.35 g., 0.76 mmole) is dissolved in a solution of hydrochloric acid in dioxane (4N, 3 ml.). After keeping the solution at room temperature for two hours, it is evaporated in vacuo to give N-[[[(3S)-3-amino-2-hydroxy-5-methylhexyl(1-methylethyl)amino]carbonyl]-L-isoleucine, methyl ester, isomer B.

(b)
N-[[[(3S)-3-[[N-[N-[(1,1-Dimethylethoxy)carbonyl]-L-phenylalanyl]-1'-[(phenylmethoxy)methyl]-L-histidyl]amino]-2-hydroxy-5-methylhexyl]-(1-methylethyl)amino]carbonyl]-L-isoleucine, methyl ester, isomer B Dicyclohexylcarbodiimide (0.161 g., 0.783 mmole) is added to a stirred (ice-bath) solution of N-[[[(3S)-3-amino-2-hydroxy-5-methylhexyl](1-methylethyl)amino]carbonyl]-L-isoleucine, methyl ester, isomer B from part (a), 1-hydroxybenzotriazole hydrate (0.12 g., 0.783 mmole), N-[N-[(1,1-dimethylethoxy)carbonyl]-L-phenylalanyl]-1'-[(phenylmethoxy)methyl]-L-histidine (0.409 g., 0.783 mmole), diisopropylethylamine (0.17 ml., 1.0 mmole), and dimethylformamide (2 ml.). Stirring is continued at 5° (cold room) overnight. It is then concentrated to dryness in vacuo and the residue is triturated with ethyl acetate and the separated dicyclohexyl urea is filtered off. The ethyl acetate solution is washed with saturated sodium bicarbonate solution and water. It is then evaporated in vacuo and the residue chromatographed (silica gel, 120 g.) using the solvent system chloroform:methanol:acetic acid (10:0.5:0.5). The product containing fractions are pooled, evaporated, and the residue is dissolved in ethyl acetate and washed with saturated sodium bicarbonate solution. The ethyl acetate solution is dried over magnesium sulfate and evaporated in vacuo to give 0.37 g. of N-[[[(3S)-3-[[N-[N-[(1,1-dimethylethoxy)carbonyl]-L-phenylalanyl]-1'-[(phenylmethoxy)methyl]-L-histidinyl]amino]-2-hydroxy-5-methylhexyl](1-methylethyl)amino]carbonyl]-L-isoleucine, methyl ester, isomer B.

(c)
N-[[[(3S)-3-[[N-[N-[(1,1-Dimethylethoxy)carbonyl]-L-phenylalanyl]-L-histidyl]amino]-2-hydroxy-5-methylhexyl](1-methylethyl)amino]carbonyl]-L-isoleucine, methyl ester, isomer B, monohydrochloride The L-isoleucine, methyl ester, isomer B product from part (b) (0.363 g., 0.42 mmole) is dissolved in methanol (10 ml.). hydrochloric acid (0.1N, 3.6 ml., prepared by diluting 1N aqueous hydrochloric acid with methanol) is added and the solution is stirred under an atmosphere of hydrogen in the presence of palladium hydroxide on carbon catalyst (100 mg.) for 18 hours. The mixture is then filtered through Celite and evaporated. After reevaporation from benzene, the residue is triturated and stirred with isopropyl ether and then filtered to give 0.30 g. of N-[[[(3S)-3-[[N-[N-[(1,1-dimethylethoxy)carbonyl]-L-phenylalanyl]-L-histidyl]amino]-2-hydroxy-5-methylhexyl](1-methylethyl)amino]carbonyl]-L-isoleucine, methyl ester, isomer B, monohydrochloride; m.p. 118°–128°; $[\alpha]_D^{20} = -50.5°$ (c=1.1, methanol). TLC (silica gel; ethyl acetate:acetic acid:water, 12:1:1) $R_f = 0.2$.

Anal. calc'd. for $C_{38}H_{61}N_7O_8 \cdot HCl \cdot 1H_2O$: C, 57.03; H, 8.06; N, 12.25; Cl, 4.43. Found: C, 57.03; H, 7.88; N, 12.04; Cl, 4.32.

EXAMPLE 7

N-[[[(3S)-3-[[N-[N-[(1,1-Dimethylethoxy)carbonyl]-L-phenylalanyl]-L-histidyl]amino]-2-hydroxy-5-methylhexyl]amino]carbonyl]-L-isoleucine, methyl ester, monohydrochloride

(a)

(S)-[3-Methyl-1-[[bis(phenylmethyl)amino]acetyl]butyl]carbamic acid, 1,1-dimethylethyl ester A solution of (S)-[3-methyl-1-[(chloromethyl)carbonyl]butyl]carbamic acid, 1,1-dimethylethyl ester (3.165 g., 12 mmole), dibenzylamine (2.31 ml., 12 mmole), sodium bicarbonate (1.52 g., 18 mmole), sodium iodide (0.9 g., 6 mmole), and dimethylformamide (24 ml.) are stirred at room temperature for one hour. An additional amount of dibenzylamine (0.23 ml., 1.2 mmole) is added and the stirring is continued for another 2.5 hours. The reaction mixture is then concentrated to dryness. The residue is taken into ethyl acetate and washed with water. The ethyl acetate solution is concentrated and on dissolution in benzene a small amount of insoluble material separates. The solution is filtered and the benzene evaporated. The residue is dissolved in ethyl acetate and passed through a small column of silica gel. The ethyl acetate solution is evaporated and the residue crystallized from hexane to give 3.603 g. of (S)-[3-methyl-1-[[bis(phenylmethyl)amino]acetyl]butyl]carbamic acid, 1,1-dimethylethyl ester; m.p. (72) 75°–77°.

(b)

(3S)-[1-[(R,S)-1-Hydroxy-2-[bis(phenylmethyl)amino]ethyl]-3-methylbutyl]carbamic acid, 1,1-dimethylethyl ester Sodium borohydride (0.354 g., 9.3 mmole) is added to a solution of (S)-[3-methyl-1-[[bis(phenylmethyl)amino]acetyl]butyl]carbamic acid, 1,1-dimethylethyl ester (3.59 g., 8.45 mmole) in ethanol (25 ml.). The solution is stirred at room temperature for one hour and then concentrated to dryness in vacuo. The residue is suspended in ethyl acetate/water and acidified to pH 2.0 using dilute hydrochloric acid. The aqueous layer is then made basic using solid sodium bicarbonate and it is extracted with ethyl acetate to give 3.65 g. of (3S)-[1-[(R,S)-1-hydroxy-2-[bis(phenylmethyl)amino]ethyl]-3-methylbutyl]carbamic acid, 1,1-dimethylethyl ester.

(c)

(3S)-[1-[(R,S)-2-Amino-1-hydroxyethyl]-3-methylbutyl]carbamic acid, 1,1-dimethylethyl ester, monohydrochloride (3S)-[1-[(R,S)-1-Hydroxy-2-[bis(phenylmethyl)amino]ethyl]-3-methylbutyl]carbamic acid, 1,1-dimethylethyl ester (4.25 g., 9.96 mmole) is dissolved in methanol (80 ml.). Aqueous hydrochloric acid (1N, 9.96 ml.) is added followed by palladium hydroxide on carbon catalyst (0.85 g.). The mixture is then stirred under an atmosphere of hydrogen for 24 hours. It is then filtered through hyflo and the solution is concentrated to dryness to give 2.62 g. of (3S)-[1-[(R,S)-2-amino-1-hydroxyethyl]-3-methylbutyl]carbamic acid, 1,1-dimethylethyl ester, monohydrochloride.

(d)

N-[[[(3S)-3-[[(1,1-Dimethylethoxy)carbonyl]amino]-2-hydroxy-5-methylhexyl]amino]carbonyl]-L-isoleucine, methyl ester N-Methylmorpholine (0.588 ml., 5.33 mmole) is added to a stirred solution of L-isoleucine, methyl ester, monohydrochloride (0.385 g., 2.12 mmole) in methylene chloride (8 ml.) at −30° followed by the dropwise addition of a solution of phosgene in benzene (12.5%, 3.18 mmole, 2.52 ml.). After stirring for 30 minutes at −20°, the mixture is concentrated to dryness in vacuo. An ice-cold solution of (3S)-[1-[(R,S)-2-amino-1-hydroxyethyl]-3-methylbutyl]carbamic acid, 1,1-dimethylethyl ester, monohydrochloride (0.6 g., 2.12 mmole) in methylene chloride (6 ml.) and N-methylmorpholine (0.47 ml., 4.24 mmole) are added to the above residue. An additional 3 ml. of methylene chloride is used for washings. The reaction mixture is stirred in an ice-bath for 2 hours and at room temperature overnight. It is then evaporated to dryness, the residue is taken up in ethyl acetate and washed with saturated sodium bicarbonate and 10% potassium bisulfate solution. The ethyl acetate extract after evaporation is chromatographed over silica gel (60 g.) using the solvent system ethyl acetate:hexane (2:1) to give 0.48 g. of N-[[[(3S)-3-[[(1,1-dimethylethoxy)carbonyl]amino]-2-hydroxy-5-methylhexyl]amino]carbonyl]-L-isoleucine, methyl ester.

(e)

N-[[[(3S)-3-Amino-2-hydroxy-5-methylhexyl]amino]carbonyl]-L-isoleucine, methyl ester, monohydrochloride The isoleucine, methyl ester product from part (d) (0.43 g., 1.03 mmole) is dissolved in a solution of hydrochloric acid in dioxane (2N, 3 ml.) and kept at room temperature for 2.5 hours. The mixture is then concentrated to dryness in vacuo to give N-[[[(3S)-3-amino-2-hydroxy-5-methylhexyl]amino]carbonyl]-L-isoleucine, methyl ester, monohydrochloride.

(f)

N-[[[(3S)-3-[[N-[N-[(1,1-Dimethylethoxy)-carbonyl]-L-phenylalanyl]-1'-[(phenylmethoxy)methyl]-L-histidyl]amino]-2-hydroxy-5-methylhexyl]amino]carbonyl]-L-isoleucine, methyl ester Dicyclohexylcarbodiimide (0.212 g., 1.03 mmole) is added to a stirred (ice-bath) solution of the L-isoleucine, methyl ester, monohydrochloride product from part (e), 1-hydroxybenzotriazole hydrate (0.158 g., 1.03 mmole), N-[N-[(1,1-dimethylethoxy)carbonyl]-L-phenylalanyl]-1'-[(phenylmethoxy)methyl]-L-histidine (0.538 g., 1.03 mmole) diisopropylethylamine (0.22 ml., 1.29 mmole), and dimethylformamide (4 ml.). Stirring is continued at 5° (cold room) overnight. The mixture is then concentrated to dryness in vacuo. The residue is triturated with ethyl acetate and the separated dicyclohexyl urea is filtered off. The ethyl acetate solution is washed with saturated sodium bicarbonate solution and water. It is then evaporated in vacuo and the residue is chromatographed over silica gel (65 g.) using the solvent system chloroform:methanol:acetic acid (10:0.75:0.75). The product containing fractions are pooled, evaporated, and the residue is dissolved in ethyl acetate and washed with saturated sodium bicarbonate solution. The ethyl acetate solution after drying over anhydrous magnesium sulfate is evaporated in vacuo to give 0.57 g. of N- [[[(3S)-3-[[N-[N-[(1,1-dimethylethoxy)carbonyl]-L-phenylalanyl-1'-[(phenylmethoxy)methyl]-L-histidyl]amino]-2-hydroxy-5-methylhexyl]amino]carbonyl]-L-isoleucine, methyl ester.

(g)
N-[[[(3S)-3-[[N-[N-(1,1-Dimethylethoxy)carbonyl]-L-phenylalanyl]-L-histidyl]amino]-2-hydroxy-5-methylhexyl]amino]carbonyl]-L-isoleucine, methyl ester, monohydrochloride The L-isoleucine, methyl ester product from part (f) (0.37 g., 0.45 mmole) is dissolved in methanol (20 ml.). Hydrochloric acid (0.1N, 4.05 ml., prepared by diluting 1N aqueous hydrochloric acid with methanol) is added and the solution is stirred under an atmosphere of hydrogen in the presence of palladium hydroxide on carbon catalyst (125 mg.) for 18 hours. The mixture is then filtered through Celite and evaporated. The residue is dissolved in isopropanol and diluted with isopropyl ether. The separated solid is filtered to give 0.27 g. of N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucine, methyl ester, monohydrochloride, m.p. 133°–158°; $[\alpha]_D^{20} = -8.0°$ (c=1.2, methanol). TLC (silica gel; ethyl acetate:acetic acid:water, 12:1:1) $R_f$=0.16.

Anal. calc'd. for $C_{35}H_{55}N_7O_8 \cdot HCl \cdot 1.5\,H_2O$: C, 54.93; H, 7.77; N, 12.82; Cl, 4.63. Found: C, 54.93; H, 7.66; N, 12.46; Cl, 4.82.

EXAMPLE 8
N-[N-[[[(3S)-3-[[N-[N-[(1,1-Dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride (a)
N-[[[(3S)-3-[[(1,1-Dimethylethoxy)carbonyl]-amino]-2-hydroxy-5-methylhexyl]amino]carbon phenylmethyl ester N-Methylmorpholine (2.5 ml., 22.73 mmole) is added to a stirred solution of L-isoleucine, phenylmethyl ester, monohydrochloride (3.56 g., 9.264 mmole) in methylene chloride (38 ml.) at −30° followed by the dropwise addition of a solution of phosgene in benzene (12.5%, 10.8 ml., 13.608 mmole). After stirring for 30 minutes at −20°, the mixture is concentrated to dryness in vacuo. A solution of (3S)-[1-[(R,S)-2-amino-1-hydroxyethyl]-3-methylbutyl]carbamic acid, 1,1-dimethylethyl ester, monohydrochloride (2.62 g., 9.264 mmole) in methylene chloride (20 ml.) is added to the above residue. While stirring the above solution in an ice-bath, N-methylmorpholine (2.0 g., 18.18 mmole) is added and the stirring is continued for 2 hours in the ice-bath and then overnight at room temperature. The mixture is then evaporated to dryness. The residue is taken up in ethyl acetate and washed neutral with sodium bicarbonate and 10% potassium bisulfate. The ethyl acetate extract after drying is chromatographed over silica gel (250 g.) using the solvent system ethyl acetate:hexane (1:1) to give 1.92 g. of N-[[[(3S)-3-[[(1,1-dimethylethoxy)carbonyl]amino]-2-hydroxy-5-methylhexyl]amino]carbonyl]-L-isoleucine, phenylmethyl ester.

(b)
N-[[[(3S)-3-[[(1,1-Dimethylethoxy)carbonyl]amino]-2-hydroxy-5-methylhexyl]amino]carbonyl]-L-isoleucine A solution of the L-isoleucine, phenylmethyl ester from part (a) (1.92 g., 3.89 mmole) in methanol (50 ml.) is stirred under an atmosphere of hydrogen for 2 hours in the presence of palladium hydroxide on carbon catalyst (0.4 g.). The mixture is then filtered through hyflo and concentrated to dryness to give 1.51 g. of N-[[[(3S)-3-[[(1,1-dimethylethoxy)carbonyl]amino]-2-hydroxy-5-methylhexyl]amino]carbonyl]-L-isoleucine.

(c)
N-[N-[(1,1-Dimethylethoxy)carbonyl]-L-phenylalanyl]-3'-[(phenylmethoxY)carbonyl]-L-histidine A solution of N-[N-[(1,1-dimethylethoxy) carbonyl]-L-phenylalanyl]-1'-[(phenylmethoxy)methyl]-L-histidine in a mixture of methanol:acetic acid (8:2, 200 ml.) is stirred under an atmosphere of hydrogen overnight in the presence of palladium hydroxide on carbon catalyst (2.6 g.). The mixture is filtered through hyflo and concentrated to dryness. The residue on crystallization from hot acetonitrile (150 ml.) gives 6.01 g. of N-[N-[(1,1-dimethylethoxy)carbonyl]-L-phenylalanyl]-L-histidine; m.p. (192) 197°–198°.

To a stirred (ice-bath) solution of N-[N-[(1,1-dimethylethoxy)carbonyl]-L-phenylalanyl]-L-histidine (3.68 g., 10 mmole) in dimethylformamide (20 ml.) and diisopropylethylamine (1.74 ml., 10 mmole) is added N-carbobenzyloxysuccinimide (3.0 g., 12 mmole). (This latter reagent is added in 4 portions at intervals of 15 minutes.) After stirring for 90 minutes, the mixture is evaporated in vacuo. The residue is taken up in ethyl acetate and washed with 10% citric acid. After evaporation of the ethyl acetate solution, the residue is chromatographed over silica gel using the solvent system chloroform:methanol:acetic acid (90:3:3) to give 3.2 g. of N-[N-[(1,1-dimethylethoxy)carbonyl]-L-phenylalanyl]-3'-[(phenylmethoxy)carbonyl]-L-histidine.

(d) 3'-[(Phenylmethoxy)carbonyl]-L-histidine, methyl ester, monohydrochloride

N-[(1,1-Dimethylethoxy)carbonyl]-L-histidine, methyl ester (2.42 g., 9 mmole) [prepared as set forth by Hanford et al., J. Org. Chem., Vol. 33, p. 251 (1968)] is dissolved in tetrahydrofuran (40 ml.) and diisopropylethylamine (1.74 ml., 9.9 mmole) is added. While stirring the above solution at room temperature, benzyloxycarbonyl chloride (1.42 ml., 9.9 mmole) is added. After a period of 90 minutes, the mixture is concentrated to dryness. The residue is taken up in ethyl acetate and washed with water. The ethyl acetate extract after evaporation is crystallized from ethyl acetate:hexane (1:1) to give 2.07 g. of N-[(1,1-dimethylethoxy)carbonyl]-3'-[(phenylmethoxy)carbonyl]-L-histidine, methyl ester.

This N-[(1,1-dimethylethoxy)carbonyl]-3'-[(phenylmethoxy)carbonyl]-L-histidine, methyl ester (1.09 g., 2.7 mmole) is dissolved in a solution of hydrochloric acid in acetic acid (2N, 24 ml.). After keeping the mixture at room temperature for 10 minutes, it is concentrated in vacuo. The residue is reevaporated from benzene and acetonitrile several times to give 3'-[(phenylmethoxy)carbonyl]-L-histidine, methyl ester, monohydrochloride.

(e)
N-[N-[[[(3S)-3-[[(1,1-Dimethylethoxy)carbonyl]amino]-2-hydroxy-5-methylhexyl]amino]carbonyl]-L-isoleucyl]-3'-[(phenylmethoxy)carbonyl]-L-histidine, methyl ester Dicyclohexylcarbodiimide (0.556 g., 2.7 mmole) is added to a stirred (ice-bath) solution of N-[[[(3S)-3-[[(1,1-dimethylethoxy)carbonyl]amino]-2-hydroxy-5-methylhexyl]amino]carbonyl]-L-isoleucine (1.09 g., 2.7 mmole), 1-hydroxybenzotriazole hydrate (0.413 g., 2.7 mmole), 3'-[(phenylmethoxy)carbonyl]-L-histidine, methyl ester, monohydrochloride (2.7 mmole), and diisopropylethylamine (0.47 ml., 2.7 mmole) in dimethylformamide (12 ml.). The reaction mixture is stirred at 5° (cold room) overnight. It is then concentrated to dryness. The residue is triturated with ethyl acetate and filtered to remove dicyclohexyl urea. The ethyl acetate solution is washed with saturated sodium bicarbonate and then evaporated. The residue is chromatographed over silica gel (200 g.) using the solvent system chloroform:methanol (95:5) to give 1.022 g. of N-[N-[[[(3S)-3-[[(1,1-dimethylethoxy)carbonyl]amino]-2-hydroxy-5-methylhexyl]amino]carbonyl]-L-isoleucyl]-3'-[(phenylmethoxy)carbonyl]-L-histidine, methyl ester.

(f)
N-[N-[[[(3S)-3-Amino-2-hydroxy-5-methylhexyl]amino]carbonyl]-L-isoleucyl]-3'-[(phenylmethoxy)carbonyl]-L-histine, methyl ester, monohydrochloride The L-histidine, methyl ester product from part (e) (0.62 g., 0.9 mmole) is dissolved in a solution of hydrochloric acid in dioxane (4N, 10.2 ml.). After keeping the mixture at room temperature for 20 minutes, it is concentrated to dryness in vacuo to give N-[N-[[[(3S)-3-amino-2-hydroxy-5-methylhexyl]amino]carbonyl]-L-isoleucyl]-3'-[(phenylmethoxy)carbonyl]-L-histidine, methyl ester, monohydrochloride.

(g)
N-[N-[[[(3S)-3-[[N-[N-[(1,1-Dimethylethoxy)carbonyl]-L-phenylalanyl]-3'-[(phenylmethoxy)carbonyl]-L-histidyl]amino]-2-hydroxy-5-methylhexyl]amino]carbonyl]-L-isoleucyl]-3'-[(phenylmethoxy)carbonyl]-L-histidine, methyl ester Dicyclohexylcarbodiimide (0.185 g., 0.9 mmole) is added to a stirred (ice-bath) solution of the L-histidine, methyl ester, monohydrochloride product from part (f) (0.9 mmole), 1-hydroxybenzotriazole hydrate (0.138 g., 0.9 mmnole), N-[N-[(1,1-dimethylethoxy)carbonyl]-L-phenylalanyl]-3'-[(phenylmethoxy)carbonyl]-L-histidine (0.483 g., 0.9 mmole), and diisopropylethylamine (0.16 ml., 0.94 mmole) in dimethylformamide (3 ml.). The reaction mixture is stirred at 5° (cold room) overnight. It is then concentrated to dryness, triturated with ethyl acetate and the separated dicyclohexyl urea is filtered off. The ethyl acetate solution is washed with saturated sodium bicarbonate and then evaporated. The residue is chromatographed over silica gel (80 g.) using the solvent system ethyl acetate:methanol (95:5) to give 0.266 g. of N-[N-[[[(3S)-3-[[N-[N-[(1,1-dimethylethoxy)carbonyl]-L-phenylalanyl]-3'-[ (phenylmethoxy)carbonyl]-L-histidyl]amino]-2-hydroxy-5-methylhexyl]amino]carbonyl]-L-isoleucyl]-3'-[(phenylmethoxy)carbonyl]-L-histidine, methyl ester.

(h)
N-[N-[[[(3S)-3-[[N-[N-[(1,1-Dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride The L-histidine, methyl ester product from part (g) (250 mg., 0.23 mmole) is dissolved in methanol (10 ml.). After adding aqueous hydrochloric acid (1N, 0.41 ml.) and palladium hydroxide on carbon catalyst (50 mg.), the solution is stirred under an atmosphere of hydrogen for 4 hours. It is then filtered through hyflo and evaporated to dryness to give 0.187 g. of N-[N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride; m.p. 75°–170°; $[\alpha]_D^{20} = -7.8°$ (c=1.7, methanol). TLC (silica gel; chloroform:methanol:acetic acid, 6:4:2) $R_f=0.7$.

Anal. cal'd. for $C_{41}H_{62}O_9N_{10} \cdot 2HCl \cdot 3.75\ H_2O$: C, 50.28; H, 7.36; N, 14.30; Cl, 7.24. Found: C, 50.30; H, 7.43; N, 14.00; Cl, 7.25.

EXAMPLES 9-29

Following the procedure of Examples 1 to 8, additional compounds within the scope of this invention can be prepared having the formula

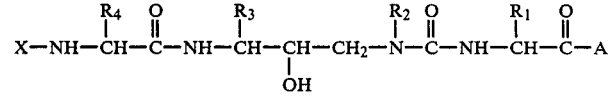

wherein the substituents are as defined below.

| Example | X | R4 | R3 | R2 | R1 | A |
|---|---|---|---|---|---|---|
| 9 | (H₃C)₃C—O—C(=O)—NH—C(=O)—CH(CH₂Ph)— | —CH₂—(imidazole) | —CH₂—Ph | —H | —CH(CH₃)(C₂H₅) | —NH—CH(CH₂Ph)—C(=O)—O—CH₃ |
| 10 | PhCH₂—O—C(=O)—NH—CH(CH₂Ph)—C(=O)— | —CH₂—(imidazole) | —CH₂—(cyclohexyl) | —H | —CH(CH₃)(C₂H₅) | —O—CH₃ |
| 11 | {—C(=O)—CH(CH₂-naphthyl)—}₂ | —CH₂—(imidazole) | —CH₂CH(CH₃)₂ | —CH₂Ph | —CH(CH₃)₂ | |
| 12 | (pyridyl)-CH₂—O—C(=O)—NH—CH(CH₂Ph)—C(=O)— | —CH₂—(indole NH) | —CH₂CH(CH₃)₂ | —H | —CH(CH₃)(C₂H₅) | —NH—CH(CH₂Ph)—C(=O)—O—CH₃ / (imidazole) |
| 13 | (H₃C)₃C—O—C(=O)—NH—CH(CH₂-cyclohexyl)—C(=O)— | —CH₂—(imidazole) | —CH₂CH(CH₃)₂ | —H | —CH(CH₃)(C₂H₅) | —NH—CH(CH₂-(indole))—C(=O)—O—CH₃ |

-continued

| Example | X | R$_4$ | R$_3$ | R$_2$ | R$_1$ | A |
|---|---|---|---|---|---|---|
| 14 | (H$_3$C)$_3$—C—O—C(=O)—NH—CH(CH$_2$-imidazole)—C(=O)— | —CH$_2$-phenyl | —CH(CH$_3$)$_2$ | —CH$_2$-cyclohexyl | —CH(CH$_3$)(C$_2$H$_5$) | —O—CH$_2$-phenyl |
| 15 | (H$_3$C)$_3$—C—O—C(=O)—NH—CH(CH$_2$-phenyl)—C(=O)— | —CH$_2$-imidazole | —CH$_2$CH(CH$_3$)$_2$ | —H | —CH$_2$-phenyl | —NH—CH(CH$_2$-imidazole)—C(=O)—O—CH$_3$ |
| 16 | (H$_3$C)$_3$—C—O—C(=O)—NH—CH(CH$_2$-phenyl)—C(=O)— | —CH$_2$-imidazole | —CH$_2$CH(CH$_3$)$_2$ | —H | —CH$_2$-pyridyl | —NH—CH(CH$_2$-phenyl)—C(=O)—O—CH$_2$-phenyl |
| 17 | (H$_3$C)$_3$—C—O—C(=O)—NH—CH(CH$_2$-phenyl)—C(=O)— | —CH$_2$-pyridyl | —CH$_2$CH(CH$_3$)$_2$ | —H | —CH(CH$_3$)(C$_2$H$_5$) | —NH—CH(CH$_2$-imidazole)—C(=O)—NH$_2$ |
| 18 | [—C(=O)—CH(CH$_2$-naphthyl)—]$_2$ | —CH$_2$-imidazole | —CH$_2$-cyclohexyl | —CH$_2$-phenyl | —CH(CH$_3$)(C$_2$H$_5$) | —NH—CH(CH$_2$-imidazole)—C(=O)—O—CH$_3$ |

| Example | X | R4 | R3 | R2 | R1 | A |
|---|---|---|---|---|---|---|
| 24 | C6H5CH2−NH−CH(CH2C6H5)−C(=O)− | −CH2−(4-imidazolyl) | −CH2CH(CH3)2 | −H | −CH(CH3)(C2H5) | −NH−CH(CH2-(4-imidazolyl))−C(=O)−OCH3 |
| 25 | (H3C)3−C−O−C(=O)− | −CH2−C6H5 | −CH2−(4-imidazolyl) | −H | −CH(CH3)(C2H5) | −NH−CH(CH2-(4-imidazolyl))−C(=O)−OCH3 |
| 26 | C6H5−SO2− | −CH2−(4-imidazolyl) | −CH2CH(CH3)2 | −H | −CH(CH3)(C2H5) | −NH−CH(CH2-(4-imidazolyl))−C(=O)−OCH3 |
| 27 | (H3C)2HCH2C−SO2− | −CH2−(4-imidazolyl) | −CH2CH(CH3)2 | −CH2CH(CH3)2 | −CH(CH3)2 | −NH−CH(CH2-(4-imidazolyl))−C(=O)−OCH3 |
| 28 | (H3C)2HCH2C−NH−C(=O)− | −CH2−(4-imidazolyl) | −CH2CH(CH3)2 | −CH2CH(CH3)2 | −CH(CH3)2 | −NH−CH(CH2−C6H5)−C(=O)−OCH3 |

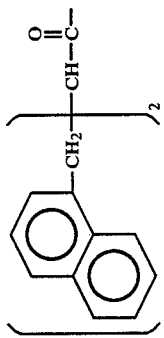

EXAMPLE 30

1000 tablets each containing the following ingredients

| | |
|---|---|
| N—[N—[[[(3S)—3-[[N—[N—[(1,1-Dimethylethoxy)carbonyl]-L-phenyl-alanyl]-L-histidyl]amino]-2-hydroxy-5-methylhexyl]amino]carbonyl]-L-isoleucyl]-L-histidine, methyl ester, dihydrochloride | 250 mg. |
| Cornstarch | 100 mg. |
| Gelatin | 20 mg. |
| Avicel(microcrystalline cellulose) | 50 mg. |
| Magnesium stearate | 5 mg. |
| | 425 mg. | are prepared from sufficient bulk quantities by mixing the N-[N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 1 to 7 and 9 to 29 can be prepared.

A similar procedure can be employed to form tablets containing 500 mg. of active ingredient.

EXAMPLE 31

An injectable solution is prepared as follows:

| | |
|---|---|
| N—[[[(3S)—3-[[N—[N—[(1,1-Dimethyl-ethoxy)carbonyl]-L-phenylalanyl]-L-histidyl]amino]-2-hydroxy-5-methylhexyl](2-methylpropyl)-amino]carbonyl]-L-valine, methyl ester, monohydrochloride (isomer A) | 1000 g. |
| Methyl paraben | 5 g. |
| Propyl paraben | 1 g. |
| Sodium chloride | 5 g. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for the product of any of Examples 2 to 29.

EXAMPLE 32

1000 Tablets each containing the following ingredients:

| | |
|---|---|
| N—[N—[[[(3S)—3-[[N—[N—[(1,1-Dimethylethoxy)carbonyl]-L-phenylalanyl]-L-histidyl]amino]-2-hydroxy-5-methylhexyl]amino]-carbonyl]-L-isoleucyl]-L-histidine, methyl ester, dihydrochloride | 500 mg. |
| Avicel | 300 mg. |
| Hydrochlorothiazide | 14.5 mg. |
| Lactose | 113 mg. |
| Cornstarch | 15.5 mg. |
| Stearic acid | 7 mg. |
| | 950 mg. | are prepared from sufficient bulk quantities by slugging the N-[N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride, Avicel, and a poriton of the stearic acid. The slugs are ground and passed through a #2 screen, then mixed with the hydrochlorothiazide, lactose, cornstarch, and remainder of the strearic acid. The mixture is compressed into 950 mg. capsule shaped tablets in a tablet press. The tablets are scored for dividing in half.

In a similar manner, tablets can be prepared containing 500 mg. of the product of any of Examples 1 to 7 and 9 to 29.

What is claimed is:

1. A compound of the formula

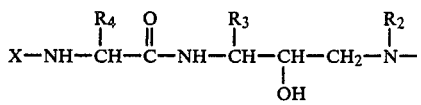

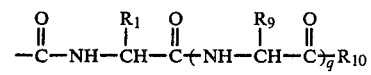

including a pharmaceutically acceptable salt thereof wherein:

X is

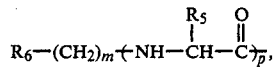

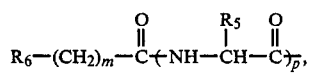

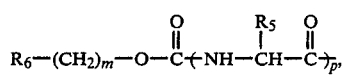

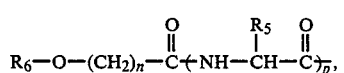

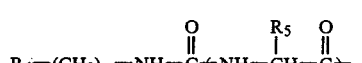

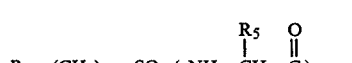

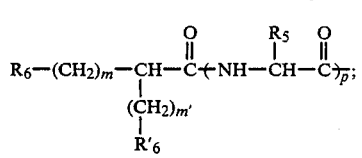

$R_1$, $R_3$, $R_4$, $R_5$, and $R_9$ are independently selected from the group consisting of hydrogen, lower alkyl, halo substituted lower alkyl, —(CH$_2$)$_n$-aryl, —(CH$_2$)$_n$-heterocyclo, —(CH$_2$)$_n$—OH, —(CH$_2$-

)$_n$—NH$_2$, —(CH$_2$)$_n$—SH, —(CH$_2$)$_n$—S-lower alkyl, —(CH$_2$)$_n$—O-lower alkyl, —(CH$_2$)$_n$—O—(CH$_2$)$_g$—OH, —(CH$_2$)$_n$—O—(CH$_2$)$_g$—NH$_2$, —(CH$_2$)$_n$—S—(CH$_2$)$_g$—OH,

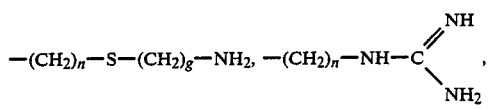

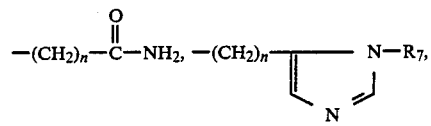

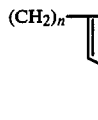

R$_2$ is hydrogen, lower alkyl, —(CH$_2$)$_m$-aryl, —(CH$_2$)$_m$-cycloalkyl, or —(CH$_2$)$_n$-heterocyclo;
R$_6$ and R'$_6$ are independently selected from the group consisting of lower alkyl, cycloalkyl, aryl and heterocyclo;
p is zero or one;
m and m' are independently selected from the group consisting of zero and an integer from 1 to 5;
n is an integer from 1 to 5;
g is an integer from 2 to 5;
R$_7$ is

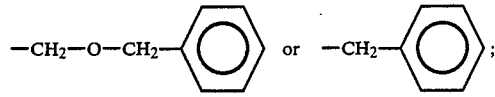

R$_8$ is 2,4-dinitrophenyl,

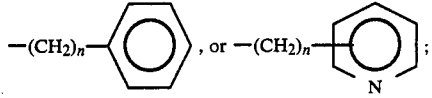

q is zero or one;
R$_{10}$ is hydroxy, —O-lower alkyl, —O—(CH$_2$)$_m$-cycloalkyl, —O—(CH$_2$)$_m$-aryl, —O—(CH$_2$)$_n$-heterocyclo, —NH$_2$, or —O-salt forming ion;
the term lower alkyl refers to straight or branched chain radicals having up to seven carbon atoms;
the term cycloalkyl refers to saturated rings of 4 to 7 carbon atoms;
the term halo refers to Cl, Br, and F;
the term halo substituted lower alkyl refers to such lower alkyl groups in which one or more hydrogens have been replaced by chloro, bromo or fluoro groups;
the term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH-alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen or hydroxy; and
the term heterocyclo refers to fully saturated or unsaturated rings of 5 or 6 atoms containing one or two O or S atoms and/or one to four N atoms provided that the total number of hetero atoms in the ring is 4 or less and bicyclic rings wherein the five or six membered ring containing O, S and N atoms as defined above is fused to a benzene ring.

2. A compound of claim 1 wherein:
X is

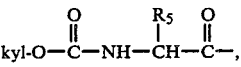

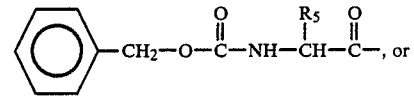

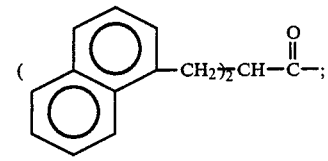

R$_1$ is lower alkyl of 3 to 5 carbons,

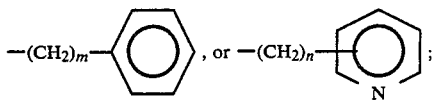

n is an integer from 1 to 3;
m is an integer from 1 to 3;
R$_2$ is hydrogen, lower alkyl of 3 to 5 carbons, —(CH$_2$)$_m$-cyclopentyl, —(CH$_2$)$_m$-cyclohexyl,

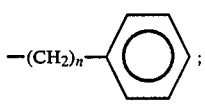

R$_3$ is lower alkyl of 3 to 5 carbons, or

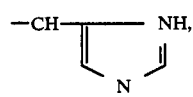

R$_4$ is

—CH——NH,
    |    ||
    N

-continued

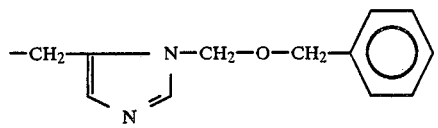

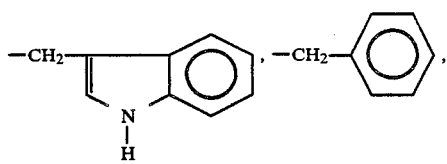

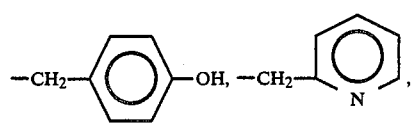

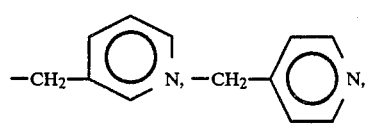

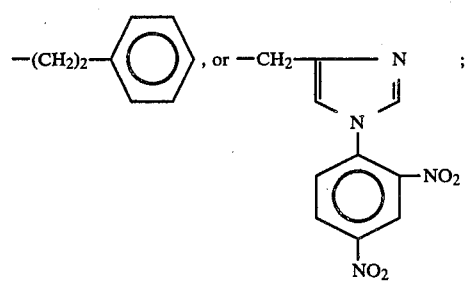

$R_5$ and $R_9$ are independently selected from the group consisting of

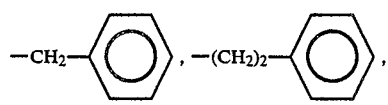

—$CH_2$—($\alpha$-naphthyl), —$CH_2$—($\beta$-naphthyl),

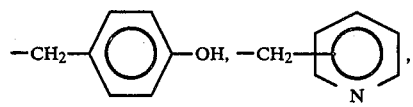

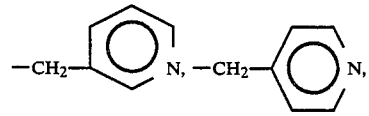

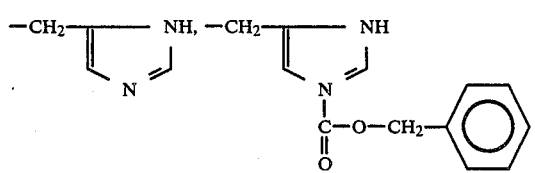

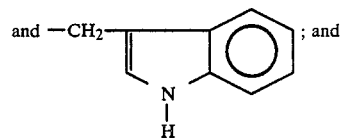

$R_{10}$ is —O—$CH_3$, —O—$C_2H_5$,

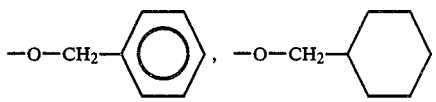

or hydroxy.

3. A compound of claim 2 wherein q is one.
4. A compound of claim 3 wherein X is

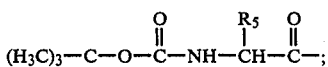

$R_1$ is

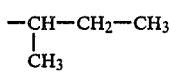

or —CH—$(CH_3)_2$;
$R_2$ is hydrogen, —$CH_2$—CH—$(CH_3)_2$, or —CH—$(CH_3)_2$;
$R_5$ is

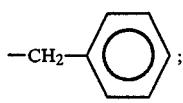

$R_4$ is

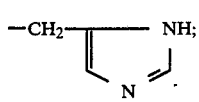

$R_3$ is —$CH_2$—CH—$(CH_3)_2$;
$R_9$ is

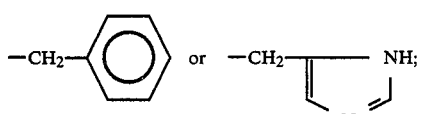

and
$R_{10}$ is —O—$CH_3$.

5. The compound of claim 4 wherein:
$R_1$ is

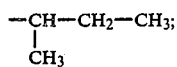

$R_2$ is hydrogen; and
$R_9$ is

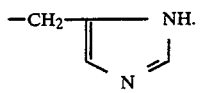

6. The compound of claim 5, N-[N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucyl]-L-histidine, methyl ester, dihydrochloride.

7. The compound of claim 4 wherein:
$R_1$ is —CH—(CH$_3$)$_2$;
$R_2$ is —CH$_2$—CH—(CH$_3$)$_2$; and
$R_9$ is

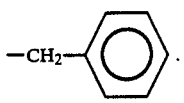

8. The compound of claim 7, N-[N-[[[(3S)-3-[[N-[N-[(1,1-dimethylethoxy)carbonyl]-L-phenylalanyl]-L-histidyl]amino]-2-hydroxy-5-methylhexyl]-(2-methylpropyl)amino]carbonyl]-L-valyl]-L-phenylalanine, methyl ester, monohydrochloride.

9. The compound of claim 4 wherein:
$R_1$ is

—CH—CH$_2$—CH$_3$;
|
CH$_3$ $R_2$ is —CH—(CH$_3$)$_2$; and
$R_9$ is

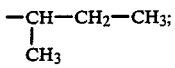

10. The compound of claim 9, N-[N-[[[(3S)-3-[[N-[N-[(1,1-dimethylethoxy)carbonyl]-L-phenylalanyl]-L-histidyl]amino]-2-hydroxy-5-methylhexyl](1-methylethyl)amino]carbonyl]-L-isoleucyl]-L-histidine, methyl ester, dihydrochloride.

11. A compound of claim 2 wherein:
q is zero.

12. A compound of claim 11 wherein X is

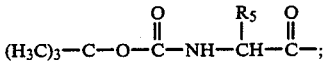

$R_1$ is

—CH—CH$_2$—CH$_3$
|
CH$_3$ or —CH—(CH$_3$)$_2$;

$R_2$ is hydrogen, —CH$_2$—CH—(CH$_3$)$_2$, or —CH—(CH$_3$)$_2$;
$R_5$ is

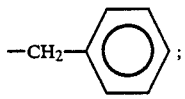

$R_4$ is

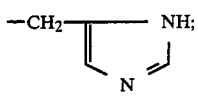

$R_3$ is —CH$_2$—CH—(CH$_3$)$_2$; and
$R_{10}$ is —O—CH$_3$.

13. The compound of claim 12 wherein:
$R_1$ is —CH—(CH$_3$)$_2$; and
$R_2$ is —CH—CH$_2$—CH—(CH$_3$)$_2$.

14. The compound of claim 13, N-[[[(3S)-3-[[N-[N-[(1,1-dimethylethoxy)carbonyl]-L-phenylalanyl]-L-histidyl]amino]-2-hydroxy-5-methylhexyl](2-methylpropyl)amino]carbonyl]-L-valine, methyl ester, monohydrochloride.

15. The compound of claim 12 wherein:
$R_1$ is

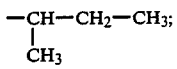

and
$R_2$ is —CH—(CH$_3$)$_2$.

16. The compound of claim 15, N-[[[(3S)-3-[[N-[N-[(1,1-dimethylethoxy)carbonyl]-L-phenylalanyl]-L-histidyl]amino]-2-hydroxy-5-methylhexyl]-(1-methylethyl)amino]carbonyl]-L-isoleucine, methyl ester, monohydrochloride.

17. The compound of claim 12 wherein:
$R_1$ is

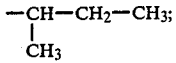

and
$R_2$ is hydrogen.

18. The compound of claim 17, N-[[[(3S)-3-[[N-[N-[(1,1-dimethylethoxy)carbonyl]-L-phenylalanyl]-L-histidyl]amino]-2-hydroxy-5-methylhexyl]amino]carbonyl]-L-isoleucine, methyl ester, monohydrochloride.

19. A composition for treating hypertension in a mammalian species comprising a pharmaceutically acceptable carrier and an anti-hypertensively effective amount of a compound of claim 1.

20. A method of treating hypertension in a mammalian species which comprises administering an anti-hypertensively effective amount of the composition of claim 19.

* * * * *